(12) United States Patent
Galinski

(10) Patent No.: US 11,583,515 B2
(45) Date of Patent: *Feb. 21, 2023

(54) COMPOSITION AND METHOD FOR RAPIDLY INDUCING AN ENDOGENOUS KETOSIS

(71) Applicant: Jesse Alexander Galinski, Temple Terrace, FL (US)

(72) Inventor: Jesse Alexander Galinski, Temple Terrace, FL (US)

(*) Notice: Subject to any disclaimer, the term of this patent is extended or adjusted under 35 U.S.C. 154(b) by 146 days.

This patent is subject to a terminal disclaimer.

(21) Appl. No.: 17/233,007

(22) Filed: Apr. 16, 2021

(65) Prior Publication Data

US 2021/0228542 A1    Jul. 29, 2021

Related U.S. Application Data

(63) Continuation of application No. 15/204,618, filed on Jul. 7, 2016, now Pat. No. 10,987,340.

(60) Provisional application No. 62/196,314, filed on Jul. 24, 2015.

(51) Int. Cl.
| | | |
|---|---|---|
| *A61K 31/385* | (2006.01) | |
| *A61K 33/10* | (2006.01) | |
| *A61K 31/198* | (2006.01) | |
| *A23L 33/00* | (2016.01) | |
| *A23L 33/16* | (2016.01) | |
| *A23L 33/175* | (2016.01) | |
| *A61K 31/02* | (2006.01) | |
| *A23L 33/10* | (2016.01) | |

(52) U.S. Cl.
CPC .......... *A61K 31/385* (2013.01); *A23L 33/10* (2016.08); *A23L 33/16* (2016.08); *A23L 33/175* (2016.08); *A23L 33/30* (2016.08); *A61K 31/02* (2013.01); *A61K 31/198* (2013.01); *A61K 33/10* (2013.01); *A23V 2002/00* (2013.01)

(58) Field of Classification Search
CPC .... A61K 31/02; A61K 31/198; A61K 31/385; A61K 33/10; A61K 2300/00; A23V 2002/00; A23V 2200/332; A23V 2250/0606; A23V 2250/1586; A23L 33/10; A23L 33/16; A23L 33/175; A23L 33/30

See application file for complete search history.

(56) References Cited

U.S. PATENT DOCUMENTS

| | | |
|---|---|---|
| 5,087,624 A | 2/1992 | Boynton et al. |
| 5,942,255 A | 8/1999 | Klesges |
| 6,224,917 B1 | 5/2001 | Murto |
| 6,277,842 B1 | 8/2001 | Carthron |
| 2002/0006907 A1 | 1/2002 | Gardiner et al. |
| 2003/0119888 A1 | 6/2003 | Allen |
| 2005/0288373 A1 | 12/2005 | Ron |
| 2006/0013903 A1 | 1/2006 | Romero et al. |

FOREIGN PATENT DOCUMENTS

WO    2014153416 A1    9/2014

OTHER PUBLICATIONS

Koopman et al., Coingestion of carbohydrate with protein does not further augment postexercise muscle protein synthesis, Jul. 3, 20074, Am J Physiol Endocrinol Metab, vol. 293, E883-E842 (Year: 2007).

*Primary Examiner* — Ali Soroush
(74) *Attorney, Agent, or Firm* — Derek Fahey, Esq.; The Plus IP Firm, PLLC

(57) ABSTRACT

A composition and method for rapidly inducing a state of endogenous ketosis, the composition including: about 26.66-28.57 percent by mass of alpha lipoic acid; about 0.01-0.02 percent by mass of chromium picolinate; about 47.61-49.99 percent by mass of L-arginine; and, about 23.33-23.81 percent by mass of calcium carbonate. The method includes restricting carbohydrate consumption to a maximum dosage of about 20 grams prior to consumption of the composition and wherein consumption of the composition is on an empty stomach. About thirty minutes after consumption of the composition the user performs moderate intensity exercise. About three hours after consuming a first dose the user tests for a presence of ketones in urine utilizing at least one sodium nitroprusside urine ketone reagent strip.

18 Claims, 4 Drawing Sheets

Racemic Alpha Lipoic Acid

Chromium Picolinate.

L-arginine.

Calcium Carbonate

COMPOSITION AND METHOD FOR RAPIDLY INDUCING AN ENDOGENOUS KETOSIS

CROSS-REFERENCE TO RELATED APPLICATIONS

This application is a continuation of U.S. patent application Ser. No. 15/204,618, entitled, "COMPOSITION AND METHOD FOR RAPIDLY INDUCING AN ENDOGENOUS KETOSIS" and filed on Jul. 7, 2016, and which claims priority from U.S. Provisional Application Ser. No. 62/196,314, entitled "AN ORAL DIETARY SUPPLEMENT THAT RAPIDLY INDUCES KETOSIS VIA GLUT PROTEIN EXPRESSION" filed on Jul. 24, 2015, the entire disclosure of which is incorporated herein.

TECHNICAL FIELD

The present invention relates generally to the field dietary supplements, and more particularly relates to supplements for promoting weight loss, preserving lean body mass, improving insulin resistance, and improving lipid profile.

BACKGROUND

Approximately 34.9% of all Americans are obese and this percentage of the United States population represents more than 78.6 million American adults. Currently, the CDC estimates that at least 70.7% of American adults over the age of twenty are overweight which is defined as a BMI of 25-29.9 with a BMI of 30 and above indicating obesity. Two of the leading causes of mortality in the United States are cardiac associated conditions and Type 2 Diabetes Mellitus, both of which have been directly linked to obesity through increased risk. The CDC estimates that the annual cost of obesity, in 2008 dollars, in the United States, exceeds more than $147 billion with obese adults requiring additional medical expenses of $1,429.00 over their non-obese adult counterparts.

World Health Organization (WHO) has stated that the obese world population has doubled since 1980. The WHO lists current world obesity statistics on their website and makes three statements concerning obesity: 1.) 42 million children were overweight or obese in 2013; 2.) More than 1.9 billion adults were overweight or obese in 2014; and, 3.) Obesity is preventable. Clearly an obesity pandemic exists, and two important questions must be considered. Why has the world overweight and obese population continued to grow even though new medical technology is continuously produced and dietary guidelines continuously updated? Why have the majority of diets recommended by health professionals failed to have an impact on the obese population or slow the growth of the overweight population? The answers to the above questions are quite complex and include not only the various etiologies of obesity itself such as genetics, medical comorbidities, lack of exercise, or simple overeating; but also a widespread, misunderstanding of fundamental human biochemistry coupled with practice and propagation, through education, of flawed nutritional principles.

Low Calorie Diets

At the very foundation of the low-calorie diet is the energy balance equation in which weight change is dependent only on calories consumed vs. calories used for metabolism, essentially calories in vs. calories out. Low-calorie or calorie-restricted diets are arguably the most practiced diet methodology in the world today and are staunchly founded in energy balance equation theory. The basic principle of any reduced calorie diet is as follows: To lose weight, specifically from fat, an individual must reduce caloric intake thereby creating a caloric deficit which the body must then make-up for by relying on its fat stores to produce the calories needed for basal energy production. For example, it is widely taught by nutrition field professionals that 1 lb. of fat contains 3,500 calories and by reducing caloric intake by 500 calories per day for 7 consecutive days an individual may lose 1 lb. of fat per week (−500 Cal/day*7 days/week=−3,500 Cal/week=−1 lb./week). Relying upon this method, an individual who wished effect a 10 lb. weight loss over a 10 week period must simply consume 3,500 fewer calories, per week, for 10 consecutive weeks creating an overall deficit of 35,000 calories. Further, the deficit required is 500 calories per day overall and calories may be cut from any major nutrient group—lipids, carbohydrates, or proteins. The reality is that the 3,500 calorie principal is nothing more than simple mathematics used to visualize the loss of a so-called pound of fat. The idea of cutting 3,500 calories from the diet to effect the loss of 1 lb. of fat could not be further from the truth when considering principals of human biochemistry and human adipose tissue composition.

The 3,500 calorie theory originated in the late 1950s by Max Wishnofsky MD, who concluded, after reviewing previous studies on the subject, that one pound of human adipose tissue contains approximately 3,500 calories of stored energy and is composed of approximately 87% lipid.

Interesting to note, is that several other researchers in the same field concluded, through similar studies, that the lipid content of human adipose tissue is highly variable and ranges anywhere from 61-94%. 1 lb. of human tissue contains 453.6 g and fat, in particular, contains 9 calories per gram. Using Wishonfskys method it can be shown that 1 lb. of adipose tissue contains approximately 3,500 calories: (453.6 g/lb.*0.87% lipid*9 Cal/g=3,551.7 Cal/lb.). However, applying the range of lipid makeup percentages to this number gives an extensive variation of how many fat calories actually make up 1 lb. of adipose tissue, 2490.3-3537.5 calories. Protein may also contribute calorically to adipose tissue and was found in studies to be roughly 1-6.5% of adipose tissue make-up. Therefore, the total caloric content of 1 lb. of human adipose tissue, accounting for lipid and protein make-up, ranges from 2508.4 Cal/lb.-3655.4 Cal/lb.

Other studies have concluded that human adipose tissue makeup is highly variable with the water, lipid, nitrogen, and protein portions being age dependent with lipid content increasing over time as the other components decrease. It is clear to see that without intimate knowledge of one's own adipose tissue makeup, simply reducing caloric intake by 3,500 calories per week could potentially result in a diet roller-coaster with unexpected results. Further, the 3,500 calorie rule assumes body weight changes linearly over time during a dieting period with steady decreases in body fat percentage. This concept of linear weight change in the form of weight loss is simply not true as both total body weight and fat composition may fluctuate up or down during dieting periods while the body attempts to adapt to the diet. Concerning the digestion of food in general, the energy balance equation simply states that to achieve optimal energy balance calories burned through metabolism must equal calories consumed. The definition of one calorie is the amount of heat required to raise the temperature of one kilogram of water one degree Celsius.

The problem with calories as they relate to nutrition is that the scientific definition as given above applies to closed systems and not human biometabolism and this is exactly the reason that 500 calories of broccoli and 500 calories of sugary soda are processed differently by the body. Throwing fuel on an already out of control fire, food industry companies often promote 100 calorie portion sized snacks as healthy due to reduced calorie content however the difference between a 100 calorie apple and a 100 calorie bag of chocolate chip cookies cannot be overlooked and to state that the two are equal is pseudoscience. Further, it is scientific fact that the digestion of protein, due to its chemical structure, requires more energy expenditure than digestion of carbohydrate or fat and this completely flies in the face of the widespread belief that a calorie is a calorie regardless of its nature.

The fallacy of the low-calorie ideology is further manifest by a 2003 publication from the Nutrition Department at Harvard's School of Public Health. The study compared the weight loss potential of various diets based on caloric intake by placing participants on one of three diets for 12 weeks: low-fat-low-calorie, low-carbohydrate-low-calorie, or low carbohydrate-high-calorie. The results of the study showed the group that lost the most weight, 23 lbs. vs. 17 lbs., was the low-carbohydrate-high-calorie group and they lost more weight while eating 25,000 more calories over then 12 week period than the low-fat-low-calorie group. Further, of the two carbohydrate groups the one that ate the most calories lost the most weight, 23 lbs. vs. 20 lbs. Clearly it can be said that dietary caloric restriction or intake is not the determining factor in either weight loss or weight gain.

The reasons that the ideology of cutting calories to lose weight has persisted are several, and include resistance to change by the nutritional community, publication of flawed principals in textbooks and on internet webpages, and lack of a thorough understanding of how the human body is known to work today. A simple internet search will suffice to show the degree to which the population at large relies upon the flawed idea of cutting 3,500 calories to lose 1 lb. of fat as numerous health and fitness websites advocate this method as a means to improving health and an example of this is that as of this writing, the Mayo Clinic and The Cleveland Clinic, two highly respected medical field institutions, teach the 3,500 calorie principal to the public through their respective websites as an adequate means of weight loss from fat.

Further, the 3,500 rule makes no provision for gender, exercise, compliance to diet, individual adipose tissue makeup, or intake of various nutrients now known to promote fat deposition such as excess refined carbohydrate. While following a reduced calorie diet many individuals lose weight initially and then subsequently hit a plateau; this plateau of decreased weight loss has been shown to be due to caloric deficit as the body slows its metabolism with caloric restriction. If calories are reduced too drastically for an extended period of time weight loss occurs in the form of broken down muscle mass due the body metabolizing protein for energy production through a process called gluconeogenesis. Important to note is that not all amino acids will yield glucose via gluconeogenesis; on average, 1.6 g of amino acids are required to synthesize 1 g of glucose. Thus, to keep the brain supplied with glucose at rate of at least 120 g/day, the breakdown of 160 to 200 g of protein (roughly 1 kg of muscle tissue) would be required.

Certain types of muscle tissue, due to their permanent nature, cannot be replaced if broken down for energy production via conversion to glucose and two of the most important types of muscle tissue, cardiac and skeletal muscle, fall into this category.

One could contend that if reducing caloric intake slows the body's metabolism and results in loss of muscle mass via protein metabolism, what is the point of cutting calories to lose weight from fat in the first place? Some of the most common side effects of cutting calories are fatigue, hunger, headache, sluggish feeling, and cold intolerance, all signs of a metabolism that has ground to a halt. From a human biochemical standpoint it can be argued that cutting calories to lose weight from fat is absolutely counterproductive to the body's normal homeostatic mechanisms.

Low-Fat Diets

A second type of diet that is commonly practiced, but flawed in the extreme, is the low-fat diet. Advocates of this diet maintain that excess dietary fat directly promotes weight gain and obesity and this is due to their belief that high fat foods such as steak, eggs, and dairy products like cheese, milk, and butter will cause vascular disease in the form of plaques that occlude arteries or be deposited as excess fat in adipose tissue. This "bad fat" idea originated in the mid-20th century when a University of Minnesota researcher by the name of Ancel Keys examined the dietary lipid intake of individuals from several countries and concluded that diets high in fat and cholesterol resulted in an increased deposition of atherosclerotic plaques and increased rates of cardiovascular disease. However, Keys conclusion and subsequent publication was shown to be flawed as he was chastised by fellow researcher Jacob Yerushalmy, among a host of critics, for limiting his findings at publication to six countries instead of including data from more than twenty countries he examined in his research. Yerushalmy showed that Keys effectively relied upon researcher bias to draw his conclusions due to the fact that when data was analyzed from all countries in Keys study there was no correlation whatsoever between lipid consumption and cardiovascular disease. Keys presented his findings to the scientific community and a further study was carried out known as the Seven Countries Study which focused on dietary fat consumption and heart disease in individuals in seven countries from four geographic regions: Northern Europe, Southern Europe, The United States, and Japan. This multi-country study concluded that excess dietary lipid intake increased the risk of cardiovascular disease and obesity secondary to lipid deposition in the vasculature. This study, like Keys previous study, was flawed for multiple reasons including how the study attempted to establish causality without even a significant correlation, although Keys denied this, and how it provides no explanation for low cardiovascular disease rates in countries that consume high amounts of dietary lipid as seen in a typical Mediterranean diet. Regardless of flaw, the study was the first of its kind and received a massive amount of media attention and helped to foster similar studies by health field entities as well as the U.S. government that reached similar conclusions.

One similar study, the Framingham Heart Study, is an ongoing study based on the previously postulated correlation between dietary lipid intake and cardiovascular disease. This study is known for identifying heart disease risk factors such as smoking, high blood pressure, lack of exercise, and high cholesterol even though the link between high cholesterol and heart disease has been criticized as being weak. The highly publicized findings of the study indicate that overweight individuals generally have higher blood cholesterol levels and are at a greater risk for heart disease. However, not highly publicized is the finding that participants who consumed more dietary cholesterol and saturated fat had overall lower blood cholesterol levels, exactly the opposite of what the study expected to find from the beginning.

Indeed, a former director of the study, Dr. William Castelli stated: "For example, in Framingham, Mass., the more saturated fat one ate, the more cholesterol one ate, the more calories one ate, the lower the person's serum cholesterol. The opposite of what one saw in the 26 metabolic ward studies, the opposite of what the equations provided by Hegsted et al and Keys et al."

Further, the Framingham study includes second and third generation offspring of the original participants and it has been clearly established that over 70% of individuals suffering from hyperlipidemia do so because of genetic inheritance alone. The question should be posed that if diseases such as familial hypercholesterolemia and other genetic dyslipidemias contribute to abnormal lipid profile and cardiovascular disease more than any other factor, including dietary lipid intake, why do health and nutrition field experts continue to warn individuals to limit their dietary lipid intake? Further, the genetic dysregulation of lipid homeostasis by the liver is exactly the reason individuals with hyperlipidemia derive the most benefit from lipid lowering drugs that inhibit the HMG-CoA reductase and PCSK9, two enzymes directly involved in cholesterol production and metabolism in the body; not by reducing dietary lipid consumption or trimming the fat off of their steak.

The end result of this type of research was a fear of dietary lipid instead of an honest effort to understand its role in human metabolism. Thus in lieu of consuming dietary fat nutritionists and physicians recommended a low-fat, high carbohydrate diet with carbohydrate content making up some 60% or more of the new recommendations. There immediately arose a huge market industry for low-fat food products, but these products came with catastrophic nutritional repercussions. Low-fat food products often have excess added sugar which has been shown to be the real cause of weight gain. Indeed, a study on the consumption of sugar intake and obesity rates in 1,700 individuals in Norfolk, UK concluded that the individuals who consumed the most sugar were 54% more likely to be obese. Further, the individuals in the study who were found to be obese misrepresented the amount of sugar they actually consumed daily through underreporting of the amount consumed. The only conclusion that can be drawn from the study is that excess sugar consumption is directly linked to obesity and the average individual does not know how much sugar they are consuming daily which results in unexpected weight gain with increased body fat percentage.

A 1999 study on low-fat diets and low-fat food products found that they were not associated with improved cholesterol levels, quite the opposite, these diets were associated with worse overall LDL (bad cholesterol) levels. In a 2015 meta-analysis of research into the low-fat diet and low-fat dietary guidelines Harcombe et al found that there was absolutely no scientific basis to the 1977 and 1983 U.S. McGovern committee guidelines cautioning individuals to refrain from or limit dietary fat intake. A similar reversal of stance has recently been adopted by the American College of Cardiology and the American Heart Association on the dietary intake of cholesterol since it was blacklisted for years by nutritionists as extremely harmful to health. A 2010 meta-analysis, of twenty-one different studies involving 347,747 patients, on the relationship between saturated fat intake and cardiovascular disease concluded that there is no evidence to suggest that saturated fat contributes to cardiovascular disease. However, in a study examining the consumption of low-fat food products and their effect on overall health the conclusion was clear: excess sugar found in low-fat diet food products contributed directly to obesity which directly increases risk of cardiovascular diseases.

One of the major problems of applied nutrition concerning any diet regimen is the compliance of dieters. This lack of compliance can easily be observed when dieting individuals experience negative diet associated symptoms such as headache, fatigue, hunger, weakness, frustration, or lack of progress and discontinue their diet. Medical field advancements have come about in the form of gastric bypass surgeries for individuals who are obese; however, these procedures are invasive and often require a basal loss of weight before it is safe for a patient to undergo surgery. Also, patients who undergo gastric bypass surgery often have lifelong complications such as dumping syndrome, chronic constipation, and malabsorption that are surgery induced secondary gastrointestinal tract manipulation. From a pharmacological standpoint, medications have been researched and formulated to aid in weight loss by speeding up metabolism to burn more calories, but virtually all medications have side effects which may negatively impact a patient's nervous system, immune system, endocrine system, or psychiatric state. Concerning medical intervention, some individuals may be afraid or intimidated by surgical procedures or drug regimens and in some instances medical intervention is recommended when it may not even be indicated.

Having discussed two major diets as well as surgical and drug intervention that healthcare professionals often prescribe and dieters willingly undertake it can plainly be seen that the current obesity pandemic will continue unless some serious intervention occurs. This intervention must occur via two pathways: 1)—Proper education of nutrition and healthcare professionals, as well as patients, on research proven causes and treatments of obesity. 2)—Application of nutritional principles or vehicles for weight loss that have been shown to be current, efficacious, and science based.

Considering the previous information there currently exists a non-traditional diet regimen, known as the low-carbohydrate or ketogenic diet, that allows an individual to lose weight from fat, spare muscle mass, and avoid common symptoms of hunger, fatigue, headache, and frustration which are associated with other diets. Important to understand is that there are multiple variations of low-carbohydrate, ketogenic diets and examples include the Atkins diet, South Beach diet, the Paleo diet, and cyclic ketogenic diet. Many individuals will argue that these diets are completely different from one another, however at the micronutrient and cellular levels all low-carbohydrate, ketogenic diets are essentially the same as all rely upon a foundation of restricting excess sugars, in the form of carbohydrates, to induce fat metabolism for weight loss. When excess dietary carbohydrate is restricted the body must find a way to compensate for energy requirements and does so thorough the production of energy intermediates known as ketones. For the purposes of this invention, any diet, regardless of specific name, that restricts carbohydrate to a minimum and results in fat metabolism with endogenous ketone production will be referred to as a ketogenic diet.

Ketogenic Diets

Under normal conditions, the body mainly depends on the metabolism of glucose to supply the energy needed for cellular function, and the required glucose is normally derived from the consumption of dietary carbohydrates. These carbohydrates can be from multiple sources and be either simple or complex such as table sugar or starch. Once ingested, carbohydrates are degraded into their respective sugars, mainly glucose, and distributed to cells across the body via the bloodstream. Cells with the aid of the hormone insulin take up glucose from the blood and convert it to an intermediate known as acetyl-CoA which is then used to produce adenosine-triphosphate (ATP), the high energy compound used by cells for metabolic function. While all cells in the body rely on glucose for immediate energy production the majority of cell types do not have the capacity to store glucose for future use. However skeletal muscle and liver cells can use glucose to form glycogen, a polymer of glucose molecules linked together and sequestered for future use. Further, glycogen stored within individual muscle cells can only be degraded and used by that cell; liver glycogen however functions as a total body reserve of glucose. This specific ability of the liver to function as a total body glycogen/glucose reserve is due to the presence of the enzyme glucose-6-phosphatase in the liver. After liver glycogen has been degraded into individual glucose molecules, glucose-6-phosphatase catalyzes the transformation of these molecules so that they can exit the liver and enter the blood stream; through this mechanism the liver works to maintain normal blood glucose levels and provide a source of glucose to all tissues as needed. Muscle and liver glycogen storage capacities vary with individual, but total body muscle glycogen storage capacity is around 400 g and the liver stores around 90-110 g. The liver functions to maintain a specific blood glucose level in order to provide cells with a constant energy source and normal blood glucose ranges from 80-100 mg/dL or about 4 g of total glucose in the blood at any given time. The brain requires around 6-7 g of glucose per hour or at least 120 g per day, and red blood cells function solely on glucose derived from the blood. As blood glucose levels fall due to utilization by tissues glycogen is degraded in the liver and glucose is released into circulation for cellular uptake. Constant output of glucose by the liver can deplete its glycogen stores quickly if not replenished through carbohydrate consumption as the liver, containing roughly 90-110 g of glycogen can only meet the body's metabolic needs for a short period of time on its own. In the fed state when the muscles and liver have stored their capacity of glycogen and ATP levels are high, excess glucose is shuttled into adipocytes and stored as fat. As the intake of carbohydrate increases beyond the body's needs muscle and liver glycogen stores stay at maximum capacity and excess dietary carbohydrate is converted into glucose and subsequently fat and stored at a higher rate. The excess production and storage of fat in adipose tissue results in obesity with its secondary comorbidities such as metabolic syndrome, diabetes, heart disease, neurodegenerative diseases, and vascular diseases. In most Western diets, the major form of dietary nutrient consumed is carbohydrate in excessive amounts. The National Academies Health and Medicine Division Food and Nutrition Board set the recommended daily allowance (RDA) and adequate intake (AI) for macronutrients in the United States and Canada and recommend an intake of 130-210 g/day of carbohydrate for men and women as well as women who are pregnant or lactating and the U.S. FDA recommends a minimum intake of 300 g. In view of these recommendations excess carbohydrate consumption in the United States is easily seen as the sugar content of the most popular size soda, the one serving, twenty ounce bottle, from two of the most popular soft drink companies contains 69 g and 79 g of sugar respectively which represents 25% or more of the total daily recommendation. Indeed, studies have shown that more than half of all individuals in the United States consume sugary drinks such as soda on a daily basis and sugary drinks have been shown to make-up the top calorie source of the average teenage diet. This overconsumption of carbohydrate correlates directly with the current obesity numbers seen in the United States and the world at large.

In periods of fasting, extended exercise, or restricted carbohydrate intake muscle and liver glycogen stores are depleted. The result of glycogen depletion, without restoration, is that the body must find a way to compensate for energy requirements and does so through hepatic beta-oxidation of stored fat with subsequent production of energy intermediates known as ketones and ketones can be used by every cell in the body for energy production purposes.

Concerning ketone production, there are three molecules generally and historically referred to as ketones or ketone bodies which are produced from beta-oxidation of fatty acids within the liver—acetone, acetoacetate (AcAc), and beta-hydroxybutyrate (BHB). However, before the function of these molecules is put forth their origin must be discussed as there currently exists a literal myriad of confusion regarding the terms ketone and ketone body.

Acetone and acetoacetate are structurally and functionally ketones according to the chemical definition of a ketone—a carbonyl carbon bound to two other hydrocarbon groups. Acetoacetate can further be classified as a ketoacid due to the fact that it contains a ketone group and a carboxyl group. Beta-hydroxybutyrate is chemically classified by structure as a carboxylic acid or hydroxyacid and referring to the compound as a ketone, ketoacid, or even ketone body is erroneous as it has no ketone component. The terms "ketone body" or "ketone bodies" have come to be widely used for purposes of referring to all three molecules as a group, however this term is archaic and somewhat confusing due to differences in both structure and function of all three molecules.

The origin of the term ketone body dates to the turn of the 20th century. In 1908 a researcher by the name of Magnus Levy discovered that diabetic or fasting patients had a fruity odor component to their breath which was characterized as that of the ketone acetone. Unknown to researchers at the time was that acetoacetate is the first ketone produced by the liver in a ketogenic state and is a highly unstable molecule which undergoes spontaneous decarboxylation to form the ketone acetone or is converted to the carboxylic acid beta-hydroxybutyrate. Early 20th century researchers did not understand the complex interaction between acetone, acetoacetate, and beta-hydroxybutyrate. However, researchers did know that diabetics suffered from severe acidosis with accompanying acetone breath and they labeled the uncharacterized substances that accumulated in the blood and urine of diabetic patients' acetone bodies. The term acetone bodies was later changed to ketone bodies because acetone is a ketone. Indeed, a 1904 publication titled Clinical Urinology details the examination of several substances in the urine of diabetics while referring to them as acetone bodies while attempting to characterize their nature and function.

Acetone bodies is a term that had its roots in earlier research related to the discovery of acetoacetate and beta-hydroxybutyrate. In 1865 acetoacetate was discovered in the urine of diabetic patients and in 1884 researchers, Minkowski and E. Kulz simultaneously discovered and isolated the substance β-oxybutyric acid, or beta-hydroxybutyric acid. Further investigation showed that mild oral supplementation of beta-hydroxybutyric acid resulted in the urinary excretion of acetoacetate and acetone and high volume supplementation of beta-hydroxybutyric acid led to the excretion of all three substances. Due to the fact that administration of beta-hydroxybutyric acid resulted in the production and excretion of acetoacetate and acetone, beta-hydroxybutyrate was thought to be the parent molecule of the three. Later Magnus Levy went on to deduce that the increased level of breath acetone present in diabetic or fasting patients was secondary to breakdown of fatty acids and occurred along with production of acetoacetate and beta-hydroxybutyrate which were measurable in the urine and blood and the three molecules became an inseparable trio for better or worse. Finally, in the 1950s researchers Kaplan and Lipmann discovered that acetoacetate was the central molecule which underwent chemical change to form acetone or beta-hydroxybutyrate, however by this time the term ketone bodies had stuck and continues to be used today.

The problem arising from utilization of the term ketone bodies has to do with the fact that because acetone, acetoacetate, and beta-hydroxybutyrate have been referred to as ketone bodies for so long beta-hydroxybutyrate has actually come to be erroneously referred to as a ketone itself. This mislabeling can be seen in the way beta-hydroxybutyrate is referred to not only as a ketone body, but as a ketone in numerous publications including scientific articles and nutrition text books, health and fitness magazines, and internet websites and this is due to the assumption that a substance with a ketone-body must naturally contain a ketone component which should be the case but it is not. Further, the mislabeling of beta-hydroxybutyrate as a ketone or ketone body is highly misleading for those individuals not familiar with the chemical structure or biological function of the molecule as these individuals automatically think that an increased blood beta-hydroxybutyrate level, regardless of the source, is indicative of a state of nutritional ketosis with all of its normally ascribed health benefits which is simply not true as will be discussed later.

For the purposes of the present invention the molecules acetoacetate and acetone will be referred to as ketones as will any other molecule meeting the chemical definition of a ketone while the molecule beta-hydroxybutyrate will be referred to as a carboxylic acid due to its chemical structure and function.

As previously mentioned, when ketone production occurs acetoacetate is the very first ketone produced and has three fates: 1)—Conversion to acetyl-CoA and entry into the citric acid cycle for energy production, 2)—spontaneous decomposition to the ketone acetone, and 3)—reversible conversion to the carboxylic acid beta-hydroxybutyrate in the presence of D-beta-hydroxybutyrate dehydrogenase when cellular NADH levels are high. Important to note here is that of the three, only acetoacetate and beta-hydroxybutyrate have significant value for energy production in the body. Further, only acetoacetate is a substrate for conversion to acetyl-CoA which enters the citric acid cycle as there is no interconversion between beta-hydroxybutyrate and acetyl-CoA and unless beta-hydroxybutyrate can become acetoacetate it holds no value for energy production.

For the purposes of the present invention the described relationship between acetoacetate and beta-hydroxybutyrate cannot be emphasized enough and this is due to the fact that only endogenous production of true ketones occurring within the liver secondary to the breakdown of the body fat facilitates weight loss with improvements in lipid profile.

For the purposes of the present invention a ketogenic state refers to a metabolic state wherein the liver produces ketones from fatty acid oxidation for energy purposes. Once acetoacetate has been produced in the liver a portion of it is converted to beta-hydroxybutyrate and acetone and these substances are released into the blood. As more and more acetoacetate, acetone, and beta-hydroxybutyrate are released into circulation the concentration of these molecules in the body rises and as state known as ketosis is reached. For the purposes of the present invention the terms "ketosis" and "nutritional ketosis" refer to a subject being in a state of endogenous ketone production with elevated blood levels of ketones in the urine, breath, or blood. Nutritional ketosis is described as a state in which all tissues capable of relying upon ketones for energy are actively doing so and typically occurs after an individual has been in a state of ketosis for one or more weeks. There are various conventional ways of measuring if an individual has entered a state of ketosis and they include analysis of urine, breath, and blood. When ketone production in the liver begins acetoacetate is the first ketone produced and as this ketone enters the blood it is filtered by the kidneys and excreted in the urine and easily measured. Therefore, it is conventionally understood that when an individual has a urine acetoacetate concentration of at least 5 mg/dL they are said to have entered a state of endogenous ketosis. A state of endogenous ketosis is also understood to have been reached when the blood concentration of beta-hydroxybutyrate rises to at least 0.5 mmol/L secondary to acetoacetate production in the liver, not because beta-hydroxybutyrate is itself a ketone. Likewise, acetoacetate is spontaneously decarboxylated to acetone and shuttled through the blood to the lungs for disposal in the breath. Non-ketogenic individuals typically have a breath acetone level of <2 ppm while breath acetone levels of ppm indicate endogenous ketogenesis if they occur in the absence of other potential false positives such as alcohol consumption. For the purposes of the present invention it is assumed that any acetone, acetoacetate, or beta-hydroxybutyrate present in the breath, urine, or blood at levels indicative of ketosis is secondary to fatty acid oxidation and ketone production in the liver. Of note is that because acetoacetate is the first ketone produced detectible concentrations of both acetone and beta-hydroxybutyrate typically lag behind measurable levels of urinary acetoacetate. This physiologic lag is the very reason that urinalysis for acetoacetate using nitroprusside urine ketone reagent strips is a speedy and inexpensive way to detect initial entry into ketosis and is the method of detecting entry into ketosis with respect to the present invention.

It is imperative to note here that the state of nutritionally induced ketosis should not be confused with Diabetic Ketoacidosis (DKA). DKA is a state experienced by diabetics who have a high blood concentration of beta-hydroxybutyrate from uncontrolled acetoacetate production in the liver with a drop in blood pH secondary to lack of insulin, infection, trauma, or other malnutrition. In contrast to the low blood beta-hydroxybutyrate levels experienced in dieting individuals those suffering from DKA may have blood beta-hydroxybutyrate levels of 25 mmol/L with accompanying electrolyte, pH, and metabolic disturbances. Confusion of DKA with nutritional ketosis is virtually impossible unless one has an incomplete understanding of either state.

A ketogenic diet is one that is high in dietary fat and low in carbohydrate with only moderate protein intake at 1-2 g/kg of body weight per day. Classically, ketogenic diets are composed of 75-85% of calories from fat, 15-25% of calories from protein, and 5-10% of calories from carbohydrate. Typically ketogenic diets require a dietary carbohydrate restriction of less than 50 g per day for a number of days for individuals to enter a state of sustained nutritional ketosis and utilize their fat stores for fuel. One of the highly researched and written about benefits of a ketogenic diet is that it allows an individual to lose weight from fat while preserving total body protein stores i.e. muscle tissue. Cox et al, in a paper on exercise performance and ketosis, concluded that a state of nutritional ketosis had the ability to increase anabolic muscle metabolism and recovery in athletes secondary to sparing protein utilization for energy production purposes. The ability to preserve total body protein while losing weight from fat has huge potential over traditional diets as the preservation of protein typically does not occur in a diet that simply cuts calories or is low in fat due to protein being converted to glucose for energy. Bergs Biochemistry, 5th edition, contains the following statement:

"Even under starvation conditions, the blood-glucose level must be maintained above 2.2 mM (40 mg/dl). The first priority of metabolism in starvation is to provide sufficient glucose to the brain and other tissues (such as red blood cells) that are absolutely dependent on this fuel. However, precursors of glucose are not abundant. Most energy is stored in the fatty acyl moieties of triacylglycerols. Recall that fatty acids cannot be converted into glucose, because acetyl-coA cannot be transformed into pyruvate. The glycerol moiety of triacylglycerol can be converted into glucose, but only a limited amount is available. The only other potential source of glucose is amino acids derived from the breakdown of proteins. However, proteins are not stored, and so any breakdown will necessitate a loss of function."

Thus preservation of total body protein can be a state that is conducive not only to weight loss from actual fat, but also recovery from medical conditions and surgeries as well as bodybuilding and sports nutrition. Another positive aspect of a ketogenic diet is that due to the high individual intake of fat and protein satiety is prolonged and hunger is not experienced while weight loss occurs. This lack of hunger is one of the strong points of a ketogenic diet due to the fact that lack of hunger makes the diet easier to complete than a typical low-calorie, or low-fat diet. Finally, ketogenic diets themselves have been shown to improve insulin resistance, improve lipid panel, and facilitate weight loss; all of which contribute to diabetes and metabolic syndrome when dysregulation occurs.

Despite the researched and reported health benefits of the ketogenic diet the major barrier that prevents individuals from maintaining a state of ketosis long enough to lose significant weight from fat are the requirements for entering ketosis and maintaining ketosis. Normally, to enter ketosis an individual must restrict carbohydrate intake to 50 g or less per day for a period of time adequate to reduce blood glucose levels and deplete glycogen stores for transition to the production of ketones for energy. The length of time required to complete the task of entering ketosis is highly variable and depends upon several factors such as individual glycogen storage capacity, metabolic rate, and exercise. For example, an individual with a low resting metabolic rate who does not exercise may be required to consume 20 g or less of carbohydrate per day to enter ketosis; individuals with higher metabolic rates may be able to consume more carbohydrate and enter ketosis while completing little or no exercise. Studies conclude that the average American consumes roughly 270 g of carbohydrate per day, although this amount is criticized as being low, in the form of breads, pastas, sodas, and other processed food. Therefore, restricting carbohydrate intake to 50 g is usually difficult for the average person with further reductions being much more difficult to achieve. Typically, a person may have to consume this low level of carbohydrate, 50 g or 20 g, for two days to a week or more to enter a ketogenic state that can be measured via the common methods which are urine, breath, or blood. This period of carbohydrate reduction with no apparent generation of measurable ketones typically produces hunger, fatigue, light-headedness, and frustration as side effects while the body switches from utilizing glucose to ketones and is the major reason individuals do not adhere to the ketogenic diet long enough to see any noticeable effect. Symptoms of transitional hypoglycemia are described as irritability, foggy-thinking, headache, fatigue, and light-headedness and are commonly experienced between day one of a restricted carbohydrate diet and initiation of ketogenesis.

As previously stated this transitional hypoglycemic state may last for days depending on how fast an individual can enter ketosis. Thus the ability for mass numbers of individuals to enter a ketogenic state is severely retarded by the duration of carbohydrate restriction required to enter ketosis and the subsequent perceived difficulties of transitioning to a ketogenic state. Another perceived difficulty of the ketogenic diet is re-entering ketosis after a carbohydrate loading day or a cheat day. Acute carbohydrate consumption after a carbohydrate depleted state can double an individual's glycogen stores which would then require several days of carbohydrate restriction to re-enter ketosis. A similar difficulty is that some individuals will be kicked out of ketosis if they consume just a few grams of carbohydrate over their limit required for maintaining ketosis while on the diet itself.

Therefore, a need exists to overcome the problems with the prior art as discussed above, and particularly for a more efficient way to enter into and maintain a ketogenic state.

SUMMARY

This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

The present invention is directed to a formulation, to an oral dietary supplement containing a combination of alpha lipoic acid, chromium picolinate, L-arginine, and calcium carbonate as active ingredients to rapidly induce a state of ketosis when accompanied with moderate exercise and carbohydrate restriction. This rapid induction of ketosis is highly beneficial for transition to a nutritional ketogenic state due to a shortened transition time. Specifically, the combination in the present invention relies upon a synergistic effect to induce a state of endogenous ketosis through intrinsic action at the cellular level.

The present invention relies upon a combination of alpha lipoic acid, chromium picolinate, L-arginine, and calcium carbonate to induce glucose uptake and disposal with glycogen depletion via increased GLUT protein expression, increased vasodilation, increased ketogenesis, increased lipolysis, and inhibition of gluconeogenesis and lipogenesis through modulation cellular pathways including IRS1, Akt, CBL, AMPK, and MAPK. The net result of the processes mentioned above is such that when the present invention is administered and moderate exercise is completed along with carbohydrate restriction total body glucose and glycogen stores are rapidly depleted resulting in a state of endogenous ketosis in only a few hours.

The present invention is a synergistic combination of alpha lipoic acid, chromium picolinate, L-arginine, and calcium carbonate which can be used to rapidly induce a state of endogenous ketosis when accompanied with carbohydrate restriction and exercise in individuals who wish to follow a ketogenic diet. This invention will drastically reduce the time required to enter an endogenous ketogenic state to only a few hours after ingestion as opposed to the normal days to weeks of restricted carbohydrate intake making the low-carbohydrate, ketogenic diet easier for individuals to maintain.

In one embodiment, the present embodiment comprises: about 26.66-28.57 percent by mass of alpha lipoic acid; about 0.01-0.02 percent by mass of chromium picolinate; about 47.61-49.99 percent by mass of L-arginine; and, about 23.33-23.81 percent by mass of calcium carbonate.

In one embodiment, the present embodiment includes a method for inducing a state of endogenous ketosis when accompanied with carbohydrate restriction by a user. The method includes restricting carbohydrate consumption; and, consuming a composition comprising: about 26.66-28.57 percent by mass of alpha lipoic acid; about 0.01-0.02 percent by mass of chromium picolinate; about 47.61-49.99 percent by mass of L-arginine; and, about 23.33-23.81 percent by mass of calcium carbonate. In one embodiment, carbohydrate restriction is in a maximum dosage of about 20 grams per day. Additionally, in one embodiment, the method is further accompanied with moderate exercise.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims. The foregoing and other features and advantages of the present invention will be apparent from the following more particular description of the preferred embodiments of the invention, as illustrated in the accompanying drawings.

BRIEF DESCRIPTION OF THE DRAWINGS

The accompanying drawings, which are incorporated in and constitute part of this specification, illustrate embodiments of the invention and together with the description, serve to explain the principles of the disclosed embodiments. The embodiments illustrated herein are presently preferred, it being understood, however, that the invention is not limited to the precise arrangements and instrumentalities shown, wherein.

DETAILED DESCRIPTION

Figure 1:
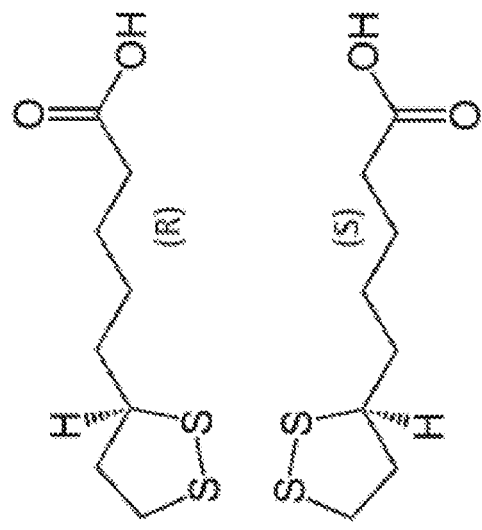
FIG. 1 is a perspective view of the molecular structure of Racemic R/S Alpha Lipoic Acid, according to an example embodiment.

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions or modifications may be made to the elements illustrated in the drawings, and the methods described herein may be modified by substituting reordering, or adding additional stages or components to the disclosed methods and devices. Accordingly, the following detailed description does not limit the disclosed embodiments. Instead, the proper scope of the disclosed embodiments is defined by the appended claims.

The disclosed invention includes a composition and methods for rapidly inducing a state of measurable endogenous ketosis. The present invention provides a physical and psychological stepping stone to maintaining a ketogenic state through carbohydrate restriction and exercise.

The present invention relates to an oral dietary supplement containing a combination of alpha lipoic acid, chromium picolinate, L-arginine, and calcium carbonate as active ingredients to rapidly induce a state of ketosis when accompanied with moderate exercise and carbohydrate restriction. This rapid induction of ketosis is highly beneficial for transition to a nutritional ketogenic state due to a shortened transition time. Specifically, the combination in the present invention relies upon a synergistic effect to induce a state of ketosis through intrinsic action at the cellular level.

A ketogenic diet is required to maintain a ketone producing state which relies upon metabolism of stored fat for energy production while preserving muscle mass. The present invention is such that it allows for rapid induction into ketosis as opposed to the normally required days to weeks of severely reduced or restricted carbohydrate intake. For the purposes of the present invention the term "rapid" as used herein refers to inducing a state of ketosis, in an individual, in only a few hours. The above described rapid induction to ketosis happens due to that fact that ketone production hinges on the bodies current carbohydrate state, loaded or depleted. In a normal individual, if the body's carbohydrate stores i.e. glycogen and glucose are at maximum capacity there will be no ketogenesis. If dietary carbohydrate is restricted, blood glucose is lowered, and glycogen stores are depleted without being replenished the result is that cells must now rely on an alternative source of fuel which is fat with subsequent ketone production.

The generalized mechanism of the present invention is activation of multiple cellular pathways that result in increased glucose and glycogen disposal and depletion, lipolysis, fatty acid oxidation, and inhibition of gluconeogenesis and lipogenesis to arrive in a state of endogenous ketone production. However, it is currently understood and accepted that all mechanisms of cellular metabolism have not been fully elucidated, and not wishing to be bound by any particular theory it is believed that the present invention will function through the interaction of several complementary mechanisms which are outlined below and which are intrinsic properties of the inventions individual components in the following ways:

Referring to FIG. 1, FIG. 1 is a perspective view of the molecular structure of Racemic R/S Alpha Lipoic Acid, according to an example embodiment. Alpha lipoic acid (ALA), or 1, 2-dithiolane-3-pentanoic acid, is a naturally occurring dithiol compound synthesized enzymatically in the mitochondrion of cells from octanoic acid. Alpha Lipoic acid is a necessary cofactor for mitochondrial alpha-ketoacid dehydrogenases and energy production and metabolism in the body. Alpha lipoic acid has two enantiomers, R and S, with the R enantiomer thought to be more absorbed and active than the S enantiomer, however, the R enantiomer is unstable without the S enantiomer present. Reports are available which indicate that supplements composed of the stabilized R enantiomer only are more expensive than racemic mixtures, possibly not as pure as claimed, and may have lower absorption therefore a racemic mixture of R and S alpha lipoic acid is utilized for the present invention. Alpha Lipoic acid in a racemic mixture of R and S enantiomers, when taken orally, has roughly a 30% bioavailability after absorption, and has been shown to have a half-life of thirty minutes to one and one half hours with complete plasma clearance in approximately three hours. In studies where individuals with impaired insulin signaling cascades received 600, 1200, and 1800 mg daily for four weeks the effectiveness of the signaling cascade on glucose uptake and utilization improved 25% and the effect of glucose uptake in individuals with intact insulin signaling cascades is even higher. The effect of supplementation of ALA is to promote reductions in blood glucose through activation of multiple cellular proteins such as IRS1, Akt, CBL, AMPK, and MAPK in the insulin receptor signaling cascade which increase glucose uptake and disposal. This modulation of the insulin signaling pathway induces cells to express proteins known as glucose transporters, i.e. GLUT proteins, on the cellular surface. Several types of GLUT proteins exist and are identified by number GLUT1, GLUT2, GLUT3 . . . etc. GLUT1 is found in highest concentrations in red blood cells and on the blood-brain barrier, GLUT2 in the liver, GLUT3 on neurons, and GLUT4 is found primarily on skeletal muscle cells. GLUT proteins function to lower blood glucose by allowing the passage of glucose into the cell to be metabolized. GLUT2 and GLUT3 proteins are insulin independent transporters. GLUT1 proteins are insulin independent, but insulin can increase their expression on the cellular surface; GLUT4 proteins are only expressed with activation of the insulin pathway or transiently activated with exercise. However, alphalipoic acid was found to induce expression and activation of GLUT1 and GLUT4 proteins independent of exercise or presence of the hormone insulin by activating the downstream insulin signaling pathway resulting in increased glucose uptake. The bioactive half-life of endogenously synthesized insulin has been reported to be approximately 5-10 minutes and in the absence of insulin pathway activation or exercise GLUT4 proteins are not expressed on cellular surfaces and are sequestered inside of the cell within storage vesicles.

The present invention induces GLUT1 and GLUT4 protein mediated glucose uptake by activating the downstream insulin signaling pathway via its alpha lipoic acid component, and due to the 1-3 hour action of alpha lipoic acid GLUT proteins may be expressed for extended periods of time, with or without exercise, leading to 40-80% increases in glucose uptake and disposal. In addition to increasing GLUT protein expression activation of cellular AMPK itself, by alpha lipoic acid, has been shown to stimulate ketogenesis, lipolysis, and fatty-acid oxidation while inhibiting lipogenesis and gluconeogenesis. By inhibiting gluconeogenesis in the liver, no new glucose can be produced from amino acids or protein catabolism which further contributes to glucose/glycogen depletion and an increased ketogenic state. Although a normal diet contains small amounts of ALA only small amounts can be absorbed in the free form from the diet, and further the amounts of ALA absorbed can be channeled to other pathways of metabolism by the body instead of promoting glucose uptake. By lowering blood glucose and expending glycogen stores, ALA has the potential to induce a ketogenic state in only a few hours when supplemented in adequate amounts and accompanied with moderate exercise and carbohydrate restriction. While ALA has the capacity to deplete glycogen and glucose over time independent of exercise, it is suggested that exercise be completed due to its additive effect at increasing GLUT protein expression which aids in decreasing the time needed to arrive in ketosis.

Figure 2:
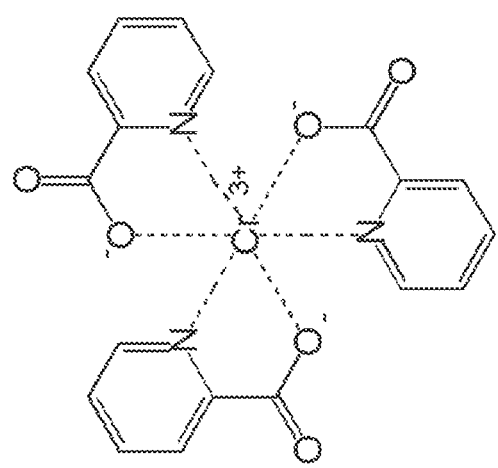
FIG. 2 is a perspective view of the molecular structure of Chromium Picolinate, according to an example embodiment.

Referring to FIG. 2, FIG. 2 is a perspective view of the molecular structure of Chromium Picolinate, according to an example embodiment. Chromium is a mineral that is required by humans for normal cellular energy metabolism. Two major forms of chromium exist trivalent (III) and hexavalent (VI) with the hexavalent form being toxic in humans. Trivalent forms of chromium include chromium nicotinate, chromium picolinate, chromium chloride, chromium polynicotinate, and chromium enriched yeast. Chromium is poorly absorbed, only about 1-2% of an ingested dose, and has been shown to have complete plasma clearance half-life 8-12 hours. Supplementation of chromium has been found to increase the rate of cellular glucose uptake several times normal with and without the presence of insulin or exercise through increased GLUT protein expression on muscle cells. Further observation has shown that the effect of chromium supplementation is activation of key proteins such as IRS1, Akt, CBL, AMPK, and MAPK, within the cell, located at and downstream of the insulin receptor; as chromium, much like lipoic acid, can act to induce increased GLUT protein expression, especially skeletal muscle GLUT4, while promoting ketogenesis, lipolysis, beta-oxidation and inhibiting gluconeogenesis, and lipogenesis.

Figure 3:
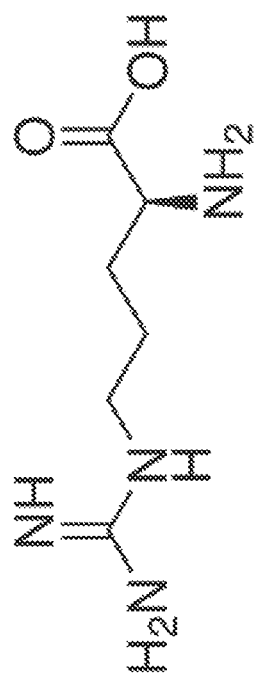
FIG. 3 is a perspective view of the molecular structure of L-arginine, according to an example embodiment; and, FIG. 4 is a perspective view of the molecular structure of Calcium Carbonate, according to an example embodiment.

Referring to FIG. 3, FIG. 3 is a perspective view of the molecular structure of L-arginine, according to an example embodiment. L-arginine, an α-amino acid, is one of the twenty most common amino acids in nature. Arginine is a conditionally essential amino acid due to the fact that it is not biosynthesized in sufficient quantities under normal conditions and is required for a limited number of metabolic reactions. Scenarios in which arginine becomes essential occur when the body's metabolism is sped up due to recovery from illness, weight loss, and anabolic muscle metabolism. Arginine is the immediate precursor to the potent vasodilator nitric oxide which exerts its effects by relaxing smooth muscle surrounding vascular tissue which results in an increased blood flow without increased blood pressure. Secondary to the increased blood flow mediated by nitric oxide is the increased delivery of nutrients to cells primarily in the form of glucose and amino acids for carbohydrate and protein metabolism. Contrary to popular belief, L-arginine has not been shown to increase the synthesis of nitric oxide during exercise and this is thought to be due to the myriad of vasodilator mechanisms already in operation in tissues during normal exercise. However, L-arginine has been shown to increase nitric oxide synthesis in resting tissues with subsequent vasodilation effects which increase nutrient delivery to tissues over time. The importance of increased vasodilation during rest cannot be stressed enough as it is an integral part of the present inventions mechanism of action. Exercising muscle tissue has been shown to have increased glucose uptake via GLUT4 proteins independent of insulin, but insulin is required for glucose uptake in resting muscle tissue. However, alpha lipoic acid and chromium mediate glucose uptake via GLUT1 and GLUT4 protein expression during periods of exercise and rest regardless of the presence of insulin and any vasodilation secondary to increased nitric oxide production from L-arginine supplementation that permits delivery of more glucose to cells from increased blood flow, at rest, speeds the glucose/glycogen disposal process itself. Along with increasing cellular glucose uptake alpha lipoic acid and chromium have both been shown to catalyze nitric oxide dependent vasodilation via increased expression of endothelial nitric oxide synthase (eNOS), the enzyme directly responsible for nitric oxide production from L-arginine.

Figure 4:
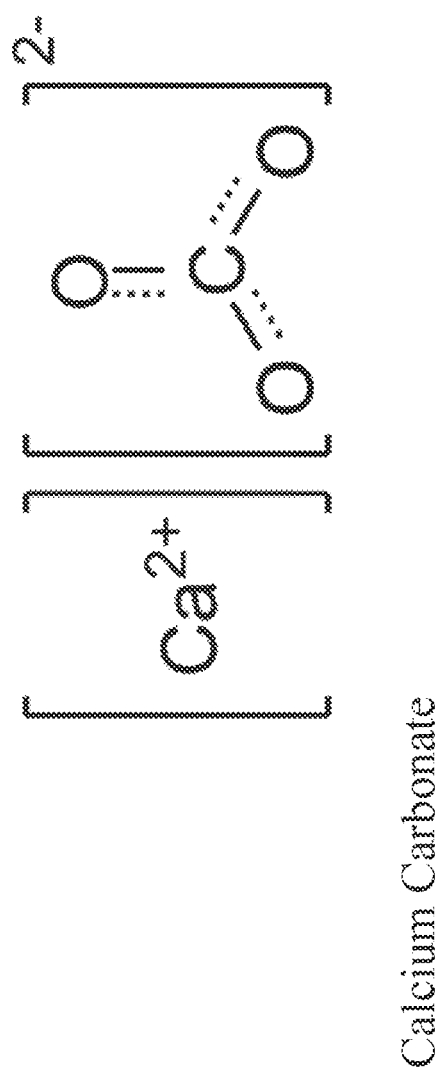

Referring to FIG. 4, FIG. 4 is a perspective view of the molecular structure of Calcium Carbonate, according to an example embodiment. Calcium Carbonate is included in the present invention and has a dual role. First, calcium carbonate may act as a gastric acid buffer ingredient as heartburn may be experienced with supplementation of any amount of alpha lipoic acid. Further, calcium is required by smooth muscle cells as a mediator in the pathway of nitric oxide smooth muscle relaxation before vasodilation occurs and multiple sources estimate that two-thirds of Americans may be calcium deficient.

It is possible for an individual to reach ketosis quickly by exercising continuously for a sufficient length of time. An individual can greatly reduce their muscle glycogen stores after 90-120 minutes of continuous high intensity exercise, such as running, and without carbohydrate consumption ketosis will eventually ensue when body glycogen is exhausted. 90-120 minutes is roughly half the time it takes a trained runner to complete a full marathon and because of this, runners typically have a carbohydrate loading day before a marathon in which carbohydrate consumption doubles their normal muscle glycogen stores allowing them to perform at high levels for extended periods of time without fatigue. It has been shown that the muscles of trained vs. untrained individuals store different amounts of glycogen. In the Sports Nutrition Guide Book it is outlined that 100 g of untrained muscle tissue can store roughly 13 g of glycogen whereas 100 g of trained or carbohydrate loaded muscle tissue may store 32-40 g of glycogen and that these stores can be depleted quickly through exercise.

For most individuals running continuously for 90-120 minutes is physiologically impossible for multiple reasons including current bill of health, age, state of overall fitness, or just pure lack of time. Highly variable studies have been conducted into the rate of glycogen utilization in tissues based on the amount of time exercised and oxygen consumed during exercise. VO2 max is a measurement of the maximum volume of oxygen an individual can consume during exercise and is related to heart rate and ability to oxidize fuels for energy production; the more conditioned an individual is the higher their VO2 max. Skeletal muscle glycogen stores have been found to be three-fourths depleted after intense exercise, 85-90 minutes with continuous cycling at 70-90% VO2 max, resulting in an oxidation of roughly 1-3 g of muscle glycogen per minute in untrained and trained individuals respectively. It has also been shown that exercise at a low VO2 max of 41% for 60 minutes resulted in complete glycogen depletion in type 1 muscle fibers and 20% depletion in type 2A muscle fibers; indeed completing some form of moderate exercise for roughly twenty minutes has been shown to decrease overall muscle glycogen stores by one-fifth and as muscle glycogen is gradually depleted muscles become fatigued and begin to rely on liver glycogen and glucose to meet energy needs.

Resting muscle cells typically rely on a ratio of carbohydrate and fat, and during exercise this ratio becomes unbalanced as 70-85% of energy production is from glycogen alone which results in rapid glycogen depletion if carbohydrates are not consumed. It is widely held that fat is the source of fuel when not exercising or exercising at low percentages of VO2 max and when an individual exercises at 55-75% of their VO2 max glycogen utilization and disposal are at maximum. The VO2 max for an average individual is between 26-52 ml·kg-1·min-1 and for the average individual exercising at 50-70% of VO2 max constitutes jogging or running. As exercising muscles burn through their glycogen stores they express GLUT4 proteins which increase the uptake of glucose from the blood and these proteins are expressed as long as exercise is occurring and a need for glucose is present. Richter et al found that increasing exercise intensity increased the number of GLUT4 proteins expressed on cellular surfaces which increased the uptake of glucose. Richter further found that glucose uptake and GLUT4 expression in exercising muscle tissue could be enhanced by independent activation of the insulin signaling pathway through modulation of proteins such as IRS1, Akt, CBL, AMPK, and MAPK, the same proteins activated by alpha lipoic acid and chromium.

As previously mentioned the liver functions as a total body glucose/glycogen reserve with a glycogen storage capacity of about 90-110 g, yet this amount of glycogen does not yield sufficient glucose to maintain normal blood glucose levels as well as supply glucose to the brain, red blood cells, and muscles for extended periods of time. Indeed, it has been stated that roughly twenty minutes of continuous exercise has the capacity to reduce muscle glycogen by one-fifth and even the loss of one-fifth of total body muscle glycogen through exercise is more than the liver has the capacity to restore if carbohydrates are not consumed shortly after exercise.

It is therefore believed that fastest way reach an endogenous ketogenic state is to empty the liver of its glycogen stores by facilitating glucose and glycogen disposal in skeletal muscles through induced and increased GLUT protein expression and when the liver has been sufficiently depleted of its glycogen it begins to oxidize fatty acids for energy with the subsequent production of ketones which then can be used for fuel. In addition, the activation of pathways involved in lipolysis and beta-oxidation promote lipid mobilization from adipose tissue to be used for energy production. Finally, the inactivation of gluconeogenic and lipogenic pathways prevents the formation of any new glucose or lipid within the body.

The present invention relies upon a combination of alpha lipoic, chromium picolinate, L-arginine, and calcium carbonate to induce glucose uptake and disposal with glycogen depletion via increased GLUT protein expression, increased vasodilation, increased ketogenesis, increased lipolysis, and inhibition of gluconeogenesis and lipogenesis through modulation cellular pathways including IRS1, Akt, CBL, AMPK, and MAPK. The net result of the processes mentioned above such that when the present invention is administered and moderate exercise is completed along with carbohydrate restriction total body glucose and glycogen stores are rapidly depleted resulting in a state of endogenous ketosis in only a few hours.

The term "about" or "approximately" as used herein refers to being within an acceptable range for the particular value as determined by one of ordinary skill in the art. The term "about" can mean within one or more standard deviations, within one or more percents, or within one or more orders of magnitude. Where individual values are described in the specification and claims the term "about" is interpreted as being within an acceptable range for the particular value.

Concentrations, amounts, solubilities, and other numerical data may be expressed or presented herein in a range format. It is understood that such a range format is used for convenience and brevity and should be interpreted flexibly to include not only the numerical values explicitly recited as the limits of the range, but also to include all the individual numerical values or sub-ranges encompassed within that range. As an illustration, a numerical range of "about 1 to about 5" should be interpreted to include not only the explicitly recited values of about 1 to about 5, but also include the individual values and sub-ranges within the indicated range.

As previously mentioned, for purposes of the present invention the terms "Ketosis" and "nutritional ketosis" as used herein refer to a subject being in a state of endogenous ketone production with ketone concentration measurable through breath, urine, or blood testing. Further, for the purposes of the present invention entry into a state of ketosis is designated as an individual having a measurable urine ketone level of at least 5 mg/dL of acetoacetate. It was previously stated that 5 mg/dL of urinary acetoacetate, 0.5 mmol/1 of blood beta-hydroxybutyrate, or >2 ppm of breath acetone are all indicators of entry into ketosis. However, the purpose of the present invention is to rapidly induce an easily measured state of ketosis and the easiest way to measure entry into an endogenous ketogenic state is urinalysis for the ketone acetoacetate and this is because measurable amounts of beta-hydroxybutyrate and acetone may lag behind measurable acetoacetate levels and require additional equipment for blood and breath analysis. Further the correlation between urine acetoacetate, blood beta-hydroxybutyrate, and breath acetone is not always clear as the levels of each may be affected by hydration, acid-base balance, and renal function. As previously stated, for the purposes of the present invention, 5 mg/dL of urinary acetoacetate as detected using nitroprusside reagent strips which detect only the ketone acetoacetate is the recommended method for detection of entry into ketosis because the test is accurate, simple to complete, inexpensive, and widely available.

The term "preferred" as applied to embodiments found herein describes the embodiment that is most suited for use by the majority of subjects due to various qualities such as ease of use, size of dose, route of administration, and efficacy at inducing the desired effect.

It is to be understood that various embodiments of the present invention may be produced without departing from the scope of the invention if they promote the mechanism of the invention by modulating the previously outline pathways and result in the desired effect, for example: L-citrulline is a direct precursor to L-arginine and studies have indicated that L-citrulline supplementation can increase L-arginine blood levels to a greater degree than L-arginine supplementation itself due to L-citrulline being taken up by the kidney and converted directly to L-arginine. The enzyme arginase is present in the liver and is highly active in metabolizing any entering L-arginine to urea which effectively reduces the amount of L-arginine available for nitric oxide production, however this does not occur with L-citrulline supplementation. The amino acid L-citrulline also has a salt form known as citrulline malate in which the malic acid portion enhances the effect of L-citrulline by increasing its absorption as well as promoting enhanced energy production in exercising muscle via exerting effects on the citric acid cycle. It is therefore understood that because L-citrulline and citrulline malate are direct precursors to L-arginine they may be substituted in the place of L-arginine if a different embodiment is desired without deviating from the proposed mechanism of nitric oxide mediated vasodilation. However, the effect of utilizing L-citrulline or citrulline malate to increase available L-arginine for subsequent nitric oxide production purposes can be dampened by the presence of various states of kidney disease, altered amino acid metabolism, or sheer amount required to produce the desired effect and as such they are not included in the preferred embodiment. Also, as mentioned previously, trivalent chromium moieties include chromium nicotinate, chromium picolinate, chromium chloride, chromium polynicotinate, and chromium enriched yeast and any of these compounds may be substituted interchangeably if a different embodiment is desired as they all exert the same effect on the IRS1, Akt, CBL, AMPK, and MAPK pathways, however the preferred embodiment contains chromium picolinate as the trivalent chromium moiety.

In any embodiment of the present invention the preferred route of administration is oral. The product may be delivered as a powdered mixture, a pre-mixed drinkable liquid, tablet, gelatin capsule, concentrated gel, or any other dosage form known to those trained in the art. The preferred embodiment of the present invention includes a combination of alpha lipoic acid, chromium picolinate, L-arginine, and calcium carbonate comprised of the following ranges of minimum weights and percents and is delivered as an orally supplemented capsule(s):

| | |
|---|---|
| Alpha lipoic acid: | 600-800 mg |
| Chromium picolinate: | 200-500 mcg |
| L-arginine: | 1000-1500 mg |
| Calcium carbonate: | 500-700 mg |
| Total weight: | 2100.2-3000.5 mg |

| Minimum percent: | |
|---|---|
| Alpha lipoic acid: | 26.66-28.57% |
| Chromium picolinate: | 0.01-0.02% |
| L-arginine: | 47.61-49.99% |
| Calcium carbonate: | 23.33-23.81% |

Production

Any embodiment of the present invention is compounded by mixing the required amounts of each ingredient in such a way that is suitable for the desired delivery method whether that be powdered mixture, a pre-mixed drinkable liquid, tablet, gelatin capsule, concentrated gel, or any other dosage form known to those trained in the art. Such embodiments may contain sweeteners, flavoring agents, coloring agents, preservatives, pharmaceutically acceptable excipients, binding agents, or lubricating agents pertaining to the delivery method desired.

Use

The term "Administration" is defined as the process in which any of the described embodiments of the present invention are delivered to an individual. Routes of administration include oral, intragastric, and parenteral. Administration of the present invention will often depend on the number of doses required to reach ketosis. One "dose" defined as the amount of any single embodiment that is sufficient to induce a state of endogenous therapeutic ketosis in the average individual. The number of administered doses required to reach ketosis may vary depending on individual weight, age, sex, duration of exercise, individual metabolic rate, and individual glycogen storage capacity.

The term "individual" is understood to encompass any member of the animal kingdom, but for the purposes of the present invention individual refers most appropriately to a human being. As used herein the term "patient" is interchangeable with "subject".

In a non-limiting example of use, an individual wishing to rapidly enter a state of ketosis may make use of the present invention in the following manor:
1. On the day an individual desires to enter a ketogenic state the individual begins by restricting dietary carbohydrate as much as possible, preferably to less than 20 g.
2. The individual self-administers one dose of the present invention on an empty stomach.
3. Thirty minutes after administration the individual performs moderate intensity exercise.
4. Three hours after administration the individual uses nitroprusside urine ketone reagent strips to test for the presence of the ketone acetoacetate in the urine.
5. If the individual's urinalysis is negative for ketone production three hours after administration of the first dose, a second dose is self-administered.
6. Beginning one hour after administration of a second dose the individual uses nitroprusside ketone reagent strips to randomly test for entry into ketosis as confirmed by a positive test.

Advantages

The present invention is useful as it would allow a significantly larger number of individuals to rapidly and easily enter a ketogenic state therefore increasing their potential to lose weight and reap the health benefits of the ketogenic diet itself 2012 statistics on the diet and weight loss supplement industry are as follows: 20 billion dollars in annual revenue were generated, 108 million people in the U.S. were on some form of diet, and 220,000 morbidly obese individuals underwent gastric bypass surgery (2009) with an $11,000-$26,000 cost per gastric bypass surgery. In 2014 the diet industry revenue was estimated to be between $20-$40 billion and surpass $60 billion by 2021. In February 2015, Wall Street Journal ran an article on the value of Atkins Nutritionals, a low-carbohydrate food producing company that was on the market for sale. In the article, the Journal estimated that Atkins Nutritionals would fetch more than $1 billion in a sale to another company. Research shows that there is a huge market for a dietary supplement that would allow rapid entry into a true endogenous ketogenic state, especially if it does not rely upon the current mechanisms of available diet supplements and has a limited side effect profile both of which make the present invention novel as compared to other supplements in general and ketogenic supplements specifically. Indeed it has been previously estimated that at least 17.2% of American households contain at least one individual on a low-carbohydrate, ketogenic diet and at least 19.2% of Americans have attempted a low-carbohydrate, ketogenic diet. Considering the current lineup of diet industry supplements for weight loss and as well as the ketogenic supplement niche, the present invention is novel for a least the following reasons:

A. Unlike other dietary supplements for weight loss the present invention does not claim to require any additional dietary consumption of carbohydrates, lipids, proteins, ketones, or stimulants to induce ketosis.
B. Unlike other dietary supplements for weight loss developed and marketed because they contain stimulants such as caffeine, green coffee bean, green tea, or synephrine that act to modulate nervous system output the present invention does not contain any stimulant nor does it induce symptoms of excess nervous system stimulation such as tachycardia, tachypnea, diaphoresis, nausea, vomiting, or fever.
C. Unlike other dietary supplements for claim to help stabilize blood glucose in healthy and/or diseased adults the present invention does not claim to stabilize blood glucose levels. In fact, the preset invention makes use of a mechanism to deplete blood glucose and glycogen to a level adequate for ketone generation, normally between 60-80 mg/dl of blood glucose.
D. Unlike other dietary supplements for weight loss that claim to be fat burners the present invention has no intrinsic mechanism to burn fat itself.
E. Unlike other dietary supplements in the same field labeled as "appetite suppressants", the present invention makes no claim to suppress, alter, or induce appetite in any way.
F. The present invention when used as directed for rapid induction to ketosis is not intended to be a daily dietary supplement. In fact, the present invention only claims to induce a state of ketosis rapidly when taken as directed whereupon the individual making use of the present invention no longer need continue supplementation if they follow a nutritional ketogenic diet. However, due to the present inventions ability to turn on specific pathways that promote glucose and glycogen disposal it is understood that the inventions use is not limited to induction of ketosis only and could theoretically be used repeatedly by an individual to help maintain a state of ketosis.
G. The present invention due to its ability to rapidly induce ketosis via glucose and glycogen disposal allows the dieter to have an occasional cheat day and not jeopardize their diet due to the fact that they can easily transition back to a ketogenic state and this type of flexibility allows the dieter to transition to a ketogenic lifestyle where they are in a state of ketosis the majority of the time.
H. Unlike other dietary supplements in the same field that claim to be carbohydrate blockers, the present invention makes no claim to block or stop the metabolism of carbohydrates in any way when carbohydrates are consumed as in a usual, carbohydrate rich diet. Consumption of excess carbohydrate will override the mechanism of the present invention to induce ketosis by replenishing glucose and glycogen stores.
I. Unlike other dietary supplements in the same field that claim to be fat blockers, the present invention does not claim to block dietary fat absorption.
J. Unlike other dietary supplements of the same field that require long-term use with multiple stage mechanisms such as "slimming stages" or "caloric restriction stage" to achieve a goal, the present invention does not rely upon long-term use with multiple stages. The present invention is a one-time, or two-time, oral supplement for rapid induction of ketosis.
K. The present invention makes no claim to treat any vitamin or mineral deficiency, disease, or medical illness.
L. The present invention if used by bodybuilders or fitness competitors offers a safe alternative to the abuse of diabetic prescription drugs, such as insulin, for quickly achieving a ketogenic state or increasing cell volumization through glucose uptake.
M. The present invention does not contain any ketones or beta-hydroxybutyrate nor does it require ingestion of either substance. Rather, the present invention induces the body to produce its own ketones endogenously via oxidation of fatty acids in the liver.
N. Because the present invention makes the claim to induce ketosis and yet contains no ketones or beta-hydroxybutyrate it stands alone as a ketogenic dietary supplement and starkly contrasts the currently marketed ketogenic diet supplements due to the fact that they contain some form of ketone, beta-hydroxybutyrate or a salt thereof, or a ketone-ester and require repeat or daily ingestion.

O. Because the present inventions mechanism is such that it claims to rapidly induce ketosis, individuals wishing to monitor their entry into ketosis can do so inexpensively through the use of nitroprusside urine ketone reagent strips sold over the counter at any pharmacy. The ability to visually reaffirm entry into ketosis via color change on ketone urine test strips promotes diet compliance.

Endogenous Ketone Production Vs. Ketone, Beta-Hydroxybutyrate Salt, or Ketone-Ester Supplementation The difference between an endogenous ketosis secondary to fatty acid oxidation occurring within the liver and supplementation of ketones, ketone esters, or carboxylic acids such as beta-hydroxybutyrate or a salt thereof deserves further attention. A stark contrast exists between the mechanism of the present invention and supplements today that are produced or marketed for their claimed effects such as inducing ketosis. The term ketosis as previously given was defined as an elevated level of ketones in the body secondary to endogenous ketone production within the liver from fatty acid oxidation. It would seem that this definition has been misconstrued to mean elevated levels of ketones in the body regardless of the source of the ketones. More specifically, elevated levels of acetoacetate or acetone after oral supplementation of beta-hydroxybutyrate or its salt form or a ketone ester. Recall that acetoacetate produced in the liver is converted to beta-hydroxybutyrate via the action of D-beta-hydroxybutyrate dehydrogenase when cellular NADH levels are high and this reaction is reversible. Also, as previously stated, beta-hydroxybutyrate only has energy value if it can be re-converted to acetoacetate. This described reversible action of the D-beta-hydroxybutyrate dehydrogenase enzyme is exactly the reason early 20th century investigators found acetone and acetoacetate in the breath and urine of those subjects who were given beta-hydroxybutyrate orally, indeed it is a normal and expected finding. It is for such reasons that comparing a ketosis secondary to supplementation of ketones, beta-hydroxybutyrate, or ketone esters to a ketosis secondary to hepatic-oxidation of fatty acids is a scenario which can only be described as the spirit of the law vs. the letter of the law. Technically, one could call both states ketosis as levels of ketones will be elevated, however the metabolic difference between an exogenous ketosis and an endogenous ketosis is astronomical.

The loss of body fat and the improvement in lipid profile is not seen with supplementation of exogenous ketone sources or beta-hydroxybutyrate salts due to the fact that supplemented ketones or beta-hydroxybutyrate salts have not been derived from acetoacetate secondary to actual fat metabolism occurring within the body. Effects of supplementation of beta-hydroxybutyrate salts were shown in a 2016 publication on the subject in which Dawley rats were given beta-hydroxybutyrate salts daily for 28 days and several health parameters were monitored including weight, lipid profile, and blood glucose. The study concluded that supplemented beta-hydroxybutyrate salts or ketone-esters had no effect on triglycerides or total cholesterol and after four weeks of repeated daily ingestion. Further, the same study found that orally supplemented beta-hydroxybutyrate salts or ketone-esters improved blood glucose numbers, but had no effect to promote weight loss and these findings are most likely attributed to their being an alternative available source of energy through conversion to acetoacetate even though glucose is present and glycogen is at maximum capacity. The study concluded that supplementation of beta-hydroxybutyrate salts or ketone-esters increases the blood level of beta-hydroxybutyrate, acetoacetate, and acetone in subjects—again a natural finding. Further the supplementation of beta-hydroxybutyrate salts or ketone-esters has been shown to only elevate blood levels beta-hydroxybutyrate, acetoacetate, or acetone for 6-8 hours after which further supplementation is required and is a far cry from the continuous production of ketones in the liver in an endogenous ketogenic state.

Through extrapolation of these facts it can clearly be seen that an exogenous state of ketosis can be induced in a subject. However the question should be posed that if an exogenous ketosis is induced through oral beta-hydroxybutyrate salts or ketone esters being metabolized directly into acetoacetate what health benefit is conveyed over endogenous ketone production? It can be argued from a valid scientific standpoint that the reason ketogenic diets are so appealing is because of their research proven health benefits such as weight loss specifically from fat and improved lipid profile and these benefits are only seen when ketone production occurs within the body and not from supplementation. Therefore claims of achieving a nutritional or therapeutic ketosis via supplementation of ketones, ketone precursors, or beta-hydroxybutyrate are misleading because they insinuate a clear health benefit of the same magnitude as an endogenous ketosis and yet provide none. It is theoretically possible that the supplementation of beta-hydroxybutyrate salts or ketone esters has the capacity to affect seizure threshold, but further studies are indicated as there are several conflicting ideas as to which molecule actually exerts an effect on the seizure threshold itself—acetoacetate, acetone, or beta-hydroxybutyrate and how the molecule should be administered.

It is for these reasons that the present invention has a clear advantage over other ketone, ketone-ester, or beta-hydroxybutyrate salt containing supplements as the present invention does not contain any exogenous ketone nor does it contain beta-hydroxybutyrate or its salt form and yet the present invention induces an endogenous ketogenic state in less than a day.

Research into Ketogenic Mechanisms

A search in PubMed, the U.S. National Library of Medicine, and National Institutes of Health returns two relevant results for "ketogenic diet pill" which are scientific, peer reviewed, publications: "The ketogenic diet in a pill: is this possible?" and "Anticonvulsant properties of an oral ketone ester in phentylenetetrazole—model of seizure."

The first article examines various novel ways of attempting to induce ketosis in individuals for neuroprotective purposes that include: modulation of the neurotransmitter GABA, supplementing ketone bodies directly, mitochondrial manipulation, decreasing reactive oxygen species, enhancing glutathione to scavenge free radicals, reducing glycolysis by restricting calories, modulating the fat hormone leptin, and supplementing polyunsaturated fats. After discussing each of the above categories the article concluded: "So the question remains, can the KD (ketogenic diet) be packaged into a pill? At this stage, given our state of knowledge, the likely answer is no." This article was published in 2009 by Rho et al. The second publication, from 2015, examines the effectiveness of a ketogenic diet on the treatment of seizure disorder by supplementing ketone esters. However, the conclusion to the article gives the status quo of scientific research on a ketogenic diet pill by stating: "This result suggests that ketone esters may pave the road towards the establishment of a ketogenic diet in a pill." This language clearly indicates that a pill which would promote an endogenous ketogenic state had not been produced as of that time.

Today, an online information website for education on Epilepsy ran an article in 2015 entitled: "Ketogenic pill to treat drug-resistant epilepsy." This article chronicled recent neuroscience research into using the drug stiripentol to mimic a ketogenic state which affects neuronal enzymatic activity in the brain and seems to be an emerging treatment for seizure disorder.

Clearly from the information provided in these resources a ketogenic diet pill would be useful in that it would have the ability to affect disease processes and such a pill is currently being sought for the same reason. However, to date, scientific research has been unable to produce an actual ketogenic pill that is efficacious at inducing endogenous ketone production without unwanted or harmful side effects and which provides all the benefits of the ketogenic state.

The present invention does not rely upon metabolic trickery through the use of prescription drugs to fool the body into believing it is in a state of ketosis. Further, the present invention does not rely upon any of the mechanisms put forward in the studies listed immediately above as potential foundations for developing a ketogenic pill. In fact, it could be inferred that the above articles teach-away from the mechanism for inducing ketosis described in the present invention through their exclusion or oversight of additional mechanisms or fields from which a ketogenic diet pill could potentially arise.

Safety of Ingredients

There is no recommended daily allowance for alpha lipoic acid and supplementation of alpha lipoic acid has been determined to be safe with no widespread serious or life-threatening reactions reported in either animal or human studies with various ranges of intake, even with large doses or extended use. Reports of rash, hives, and itching have been associated with the use of any amount alpha lipoic acid as well as transient nausea, abdominal pain, and malodorous urine. There have also been reports of alpha lipoic acid interfering with biotin absorption pathways resulting in decreased biotin absorption. Finally, there has been one scientific publication on alpha lipoic acid interacting with thyroid replacement drugs and individuals requiring thyroid hormone replacement should consider further investigation into the interaction. Alpha Lipoic Acid has also recently been found to be safe for pregnant women as a 2014 study on the use of alpha lipoic acid for treating peripheral neuropathy during pregnancy concluded that alpha lipoic acid exerted no harmful effect on mother or child.

There is currently no recommended daily allowance for chromium, however there are minimum intakes required for normal energy metabolism and they range from 25-35 mcg/day for both men and women. The supplementation of chromium has been considered safe and doses of up to 1000 mcg of chromium containing supplements have been used without any reported adverse effects.

A suggested intake, or tolerable upper limit, for L-arginine has not been established, but the maximum dose considered safe is 6,000 mg/day and this supplement would provide 1000 mg per dose.

Calcium carbonate is 40% calcium by weight and the recommended daily allowance for males and females 18 years and older is 1300 mg/day, which this supplement would provide 200-280 mg of elemental calcium per dose.

Testing and Statistics

Two trials were conducted to examine the time required for the average individual to reach a state of endogenous ketosis through dietary carbohydrate restriction combined with one round of exercise and to determine whether or not administration of the present invention was able to speed this process. Ten subjects participated in the first trial and additional sixteen subjects participated in the second trial.

Trial 1 was designed to estimate the average time required to reach a state of endogenous ketosis through dietary carbohydrate restriction and one round of exercise and the trial was used as a benchmark for comparison to results from trial two. Participants were selected on a volunteer basis with selection and testing occurring during July-September 2015. Participants were of both sexes, ranged in age from 28-66, and were screened for current state of health and excluded if they had any history of diabetes or kidney disease or were currently taking any medication which would register a false positive on urine acetoacetate nitroprusside reagent strips. Leading up to the trial, subjects consumed their normal diet and on the morning of the first day of the trial subjects completed a urinalysis to ensure they were not in a state of ketosis. No test subjects were found to be in a state of ketosis and all subjects began the test sequence by restricting total dietary carbohydrate to 20 g or less per day and completing one round of moderate intensity aerobic exercise of their choice. Moderate intensity aerobic exercise may mean when a subject is working hard enough to raise the subject's heart rate and break into a sweat. Moderate exercise may be walking briskly (3 miles per hour or faster, but not race-walking), water aerobics, low-intensity weight training, bicycling slower than 10 miles per hour, tennis (doubles), ballroom dancing, or general gardening. Subjects completed exercise routines for at least twenty minutes, but subjects were not restricted from exercising longer than twenty minutes if they wished. After completion of exercise random urinalysis was conducted to check for the presence of the ketone acetoacetate which, if present, in concentrations of at least 5 mg/dL indicated a state of endogenous ketosis. When a subject registered a positive urine ketone test the time was recorded and the trial was concluded for that subject. Table 1 below details the results from trial 1.

TABLE 1

Investigation into the average time needed for subjects to reach ketosis through carbohydrate restriction (≤20 g/24 hr) and one round of exercise.

| Subject Number | Sex | Exercise Time (Min) | Time to Ketosis (Min) | Time to Ketosis (HR) |
|---|---|---|---|---|
| 1 | M | 40 | 3135 | 52 |
| 2 | F | 36 | 2576 | 42 |
| 3 | F | 75 | 3157 | 52 |
| 4 | M | 35 | 3487 | 58 |
| 5 | M | 83 | 1786 | 29 |
| 6 | M | 60 | 2488 | 41 |
| 7 | M | 34 | 1498 | 24 |
| 8 | F | 25 | 3225 | 53 |
| 9 | F | 22 | 4093 | 68 |
| 10 | M | 60 | 2178 | 36 |
| Average | 60% Male 40% Female | 47 | 2762.3 | 45.5 |

Summary: The average time required for men and women to enter ketosis through restriction of dietary carbohydrate and one round of exercise was 2762.3 minutes (SD = 803.31), 95% CI [2188, 3337] or 45.5 hours (SD = 13.85), 95% CI [35.79, 55.21] and the average time spent exercising was 47 minutes (SD = 21.10).

Trial 2 consisted of a double-blind, placebo controlled study to determine whether or not the present invention could reduce the time it took for the average person to enter a state of ketosis based on results from trial 1. The ten subjects from trial 1 were carried over and an additional sixteen new subjects participated in trial 2 bringing the total to 26 participants. The new subjects were selected during the months of March and April 2016 and testing occurred during May 2016. Participants were of both sexes, ranged in age from 20-85, and were screened for a history of diabetes or kidney disease or use of any medication which would register a false positive on urine acetoacetate nitroprusside reagent strips and were not allowed to participate if they met any of the criteria for exclusion. Subjects were assigned a number and randomly allocated to one of two study groups. Once sorted into a group each participant was randomly assigned to one of two sub-categories: placebo or therapy.

Leading up to the day of the study the subjects were allowed to consume their normal diet. On the day of the study subjects began by restricting dietary carbohydrate as much as possible. All subjects were allowed to eat, but subjects who chose to consume meals consumed 20 g or less of total carbohydrate prior to beginning the testing sequence. All subjects fasted for two hours prior to administration of the placebo or therapy so as to have an empty stomach to increase absorption of the therapy for the subjects who received it. During the trial period subjects underwent urinalysis multiple times for the presence of ketones utilizing nitroprusside reagent strips which detect the presence of acetoacetate in the urine and a state of ketosis was considered reached when the reagent strips indicated a urinary concentration of least 5 mg/dL of acetoacetate.

Immediately before beginning the testing sequence an initial urinalysis was completed to ensure that subjects were not in a state of ketosis and subjects who were found to be in a state of ketosis were excluded from participating further. After the initial urinalysis was complete the placebo or therapy was administered orally. The placebo consisted of 1000 mg of calcium carbonate. The therapy consisted of an embodiment of the present invention containing 800 mg of alpha lipoic acid, 200 mcg of chromium picolinate, 500 mg of calcium carbonate, and 1000 mg of L-arginine. Thirty minutes after receiving the placebo or therapy subjects completed one round of moderate intensity aerobic exercise of their choice, with the exception of an 85 year old female who completed no exercise. As above, moderate intensity aerobic exercise may mean when a subject is working hard enough to raise the subject's heart rate and break into a sweat. Moderate exercise may be walking briskly (3 miles per hour or faster, but not race-walking), water aerobics, low-intensity weight training, bicycling slower than 10 miles per hour, tennis (doubles), ballroom dancing, or general gardening. All exercise routines lasted for a minimum of twenty minutes, however subjects were not discouraged from exercising for longer than twenty minutes if they wished. Exactly 180 minutes (3 hours) after administration of the placebo or therapy subjects were tested via urinalysis for the presence of ketones. If the subject tested positive the time to ketosis was recorded as 180 minutes (3 hours) and the test was complete. At the end of 180 minutes (3 hours) if a subject had not registered a positive urine ketone test a second dose of the placebo or therapy was administered. Exercise was not completed after a second administration of the placebo or therapy. Random urinalysis was completed when subjects could micturate for the next six hours and the time to ketosis was recorded if subjects had a positive urine ketone test. At the end of the six hour time period the test was complete for all subjects.

Tables 2-5 below detail the results of trial 2. Tables 2 and 3 below detail the data of the two randomized groups receiving placebos or therapy and represent groups 1 and 2 respectively. Table 4 details the specific data of subjects who completed trials 1 and 2. Table 5 details the specific data of those who participated in trial 2 only.

TABLE 2

Investigation into the average time needed to reach ketosis through administration of the present invention, dietary carbohydrate restriction, and one round of exercise group 1.

| Subject Number | Sex | Control Urine Test | $1^{st}$ dose Therapy Vs. Placebo | Exercise Time (Min) | 180 Minute Urinalysis | $2^{nd}$ Dose Therapy Vs. Placebo | Time to Ketosis after $2^{nd}$ Dose (Min) | Total In Ketosis | Total Time to Ketosis (Min) | Total Time to Ketosis (HR) |
|---|---|---|---|---|---|---|---|---|---|---|
| 1 | F | — | P | 60 | — | P | P | 0 | P | P |
| 2 | M | — | P | 57 | — | P | P | 0 | P | P |
| 3† | M | — | T | 22 | + | | | 1 | 180 | 3 |
| 4 | F | — | T | 40 | — | T | 345 | 1 | 345 | 5 |
| 5† | F | — | T | 80 | — | T | 322 | 1 | 322 | 5 |
| 6 | M | — | T | 55 | + | | | 1 | 180 | 3 |
| 7† | F | — | T | 20 | — | T | 568 | 1 | 568 | 9 |
| 8 | F | — | T | 120 | — | T | 310 | 1 | 310 | 5 |
| 9 | F | — | T | 46 | — | P | P | 0 | PP | P |
| 10† | M | — | T | 60 | + | | | 1 | 180 | 3 |
| 11† | M | — | P | 46 | — | T | 331 | 1 | 331 | 5 |
| 12 | F | — | T | 120* | * | * | * | * | ** | * |
| 13 | M | — | T | 81 | + | | | 1 | 1803 | 3 |
| Average | 46% Male 54% Female | | | 58.34 | 4 | | 5 | 9 | 288.62 | 4.55 |

P = Placebo, T = Therapy.

*Subject dropped out and data was not included in final analysis.

† Indicates subject also participated in trial one.

Summary: Of thirteen subjects randomized to study group one, twelve subjects completed the full study while one subject was discarded due to dropping out for personal reasons. Of the twelve subjects who completed the full study three subjects did not enter ketosis while nine subjects did enter ketosis. The three subjects who did not enter ketosis received placebos. Of the nine subjects who did enter ketosis four were found to be in state of ketosis after one dose and five subjects required two doses to enter ketosis. For those who did enter ketosis the average time spent exercising was 58.3 minutes (SD = 31.86) and the average time to ketosis was found to be 288.44 minutes (SD = 128.35min), 95% CI [189.8, 387.1] or 4.55 horns (SD=1.94), 95% CI [3.06, 6.04].

TABLE 3

Investigation into the average time needed to reach ketosis through administration of the present invention, dietary carbohydrate restriction, and one round of exercise group 2.

| Subject Number | Sex | Control Urine Test | 1st dose Therapy Vs. Placebo | Exercise Time (Min) | 180 Minute Urinalysis | 2nd Dose Therapy Vs. Placebo | Time to Ketosis after 2nd Dose (Min) | Total In Ketosis | Total Time to Ketosis (Min) | Total Time to Ketosis (HR) |
|---|---|---|---|---|---|---|---|---|---|---|
| 14† | M | (−) | T | 45 | (−) | T | 318 | 1 | 318 | 5 |
| 15 | F | (−) | P | 56 | (−) | P | P | 0 | P | P |
| 16 | F | (−) | T | 60 | (+) | | | 1 | 180 | 3 |
| 17† | F | (−) | T | 58 | (+) | | | 1 | 180 | 3 |
| 18 | F | (−) | T | 30 | (−) | T | 240 | 1 | 240 | 4 |
| 19 | F | (−) | T | 60 | (−) | P | P | 0 | P | P |
| 20 | M | (−) | T | 45 | (+) | | | 1 | 180 | 3 |
| 21† | M | (−) | T | 78 | (+) | | | 1 | 180 | 3 |
| 22* | M* | (+)* | * | * | * | * | * | * | * | * |
| 23† | M | (−) | P | 35 | (+) | | | 1 | 180 | 3 |
| 24† | F | (−) | T | 30 | (+) | | | 1 | 180 | 3 |
| 25 | M | (−) | T | 56 | (+) | | | 1 | 180 | 3 |
| 26 | F | (−) | T | 0 | (−) | T | 315 | 1 | 315 | 5 |
| Average | 46% male 54% Female | | | 43.7 | 7 | | 3 | 10 | 213.3 | 3.5 |

P = Placebo, T = Therapy.

*Subject was excluded from participating due to positive control urinalysis and data was not included in final analysis.

† Indicates subject also participated in trial one. Summary: Of the thirteen subjects randomized to study group two, twelve subjects completed the full study while one subject was disqualified due to a positive control ketone test. Of the twelve subjects that completed the full study two subjects did not enter ketosis while eight subjects did enter ketosis. The two subjects who did not enter ketosis received placebos. Of the ten subjects that did enter ketosis seven subjects were found to be in a state of ketosis after one dose and the remaining three subjects entered ketosis after two doses were administered. For those who did enter ketosis the average time spent exercising was 43.7 minutes (SD = 21.50) and the average time to ketosis was 213.3 minutes (SD =57.52), 95% CI [172.2, 254.4] or 3.5 hours (SD = 0.85), 95% CI [2.89, 4.11].

TABLE 4

Investigation into the average time needed to reach ketosis when using the present invention for subjects who also completed trial 1.

| Subject Number | Sex | Control Urine Test | 1st dose Therapy Vs. Placebo | Exercise Time (Min) | 180 Minute Urinalysis | 2nd Dose Therapy Vs. Placebo | Time to Ketosis after 2nd Dose (Min) | Total In Ketosis | Total Time to Ketosis (Min) | Total Time to Ketosis (HR) |
|---|---|---|---|---|---|---|---|---|---|---|
| 14† | M | (−) | T | 45 | (−) | T | 318 | 1 | 318 | 5 |
| 3† | M | (−) | T | 22 | (+) | | | 1 | 180 | 3 |
| 7† | F | (−) | T | 20 | (−) | T | 568 | 1 | 568 | 9 |
| 17† | F | (−) | T | 58 | (+) | | | 1 | 180 | 3 |
| 10† | M | (−) | T | 60 | (+) | | | 1 | 180 | 3 |
| 11† | M | (−) | P | 46 | (−) | T | 331 | 1 | 331 | 5 |
| 5† | F | (−) | T | 81 | (−) | T | 322 | 1 | 322 | 5 |
| 21† | M | (−) | T | 78 | (+) | | | 1 | 180 | 3 |
| 23† | M | (−) | P | 35 | (+) | | | 1 | 180 | 3 |
| 24† | F | (−) | T | 30 | (+) | | | 1 | 186 | 3 |
| Average | 40% Male 60% Female | | | 47.5 | 6 | | 4 | 10 | 261.9 | 4.2 |

P = Placebo, T = Therapy.

† Indicates subject also participated in trial one.
Summary: Analysis of subjects who completed trials 1 and 2. In both trials all ten subjects reached a state of ketosis however the time needed to reach a state of ketosis was drastically reduced in trial 2 with the only difference being administration of the present invention. In trial 2 these subjects exercised for an average of 47.5 minutes (SD = 21.59) and reached a state of ketosis in an average time of 261.9 minutes (SD = 127.12), 95% CI [171,352.8] or 4.2 hours (SD = 1.93), 95% CI [2.82, 5.58].

TABLE 5

Investigation into the average time needed to reach ketosis when using the present invention for subjects who did not complete trial 1.

| Subject Number | Sex | Control Urine Test | 1st dose Therapy Vs. Placebo | Exercise Time (Min) | 180 Minute Urinalysis | 2nd Dose Therapy Vs. Placebo | Time to Ketosis after 2nd Dose (Min) | Total In Ketosis | Total Time to Ketosis (Min) | Total Time to Ketosis (HR) |
|---|---|---|---|---|---|---|---|---|---|---|
| 25 | M | (−) | T | 56 | (+) | | | 1 | 180 | 3 |
| 26 | F | (−) | T | 0 | (−) | T | 315 | 1 | 315 | 5 |
| 20 | M | (−) | T | 45 | (+) | | | 1 | 180 | 3 |
| 18 | F | (−) | T | 30 | (−) | T | 240 | 1 | 240 | 4 |
| 16 | F | (−) | T | 60 | (+) | | | 1 | 180 | 3 |
| 13 | M | (−) | T | 81 | (+) | | | 1 | 180 | 3 |
| 8 | F | (−) | T | 120 | (−) | T | 310 | 1 | 310 | 5 |
| 6 | M | (−) | T | 55 | (+) | | | 1 | 180 | 3 |
| 4 | F | (−) | T | 40 | (−) | T | 345 | 1 | 345 | 5 |
| Average | 44.4% Male 55.5% Female | | | 54.1 | 5 | | 4 | 9 | 234.4 | 3.77 |

P = Placebo, T = Therapy.

† Indicates subject also participated in study 1

Summary: Analysis of subjects who completed trial 2 only and were not involved in trial 1. Subjects completed exercise for an average time of 54.1 minutes (SD = 33.3) and reached a state of ketosis in 234.4 minutes (SD = 70.1), 95% CI [180.5, 288.3] or 3.77 hours (SD = 0.92), 95% CI [3.063, 4.477]. Of note is that subject #26, an 85 year old female, received two doses of the present invention and entered ketosis in 5 hours without completing any exercise.

Results

Data analysis was conducted for the various studies with alpha criterion set at <0.05, the conventional level used to accept or reject data based on statistical significance. A paired samples t-test of subjects completing trial 1 and trial 2 (data from tables 1 and 4) was conducted to evaluate the time required to enter ketosis after completing exercise and restricting dietary carbohydrate vs. subjects completing exercise, restricting dietary carbohydrate, and receiving the present invention. There was a statistically significant difference revealed which was a decrease in mean time required for subjects to enter ketosis from trial 1 (M=45.5, SD=13.85) to trial 2 (M=4.2, SD=1.93), t(9)=9.4635, p<0.0001 (two-tailed) with the difference in the means from trial 1 to trial 2 being 41.30 (hours) 95% CI [31.43,51.17]. A 41.30 hour reduction in the mean time required to enter ketosis from trial 1 to trial 2 represents a roughly 90% decrease in the total time required to reach ketosis when the present invention is used in combination with exercise and carbohydrate restriction as opposed to dietary carbohydrate restriction and exercise alone.

A paired samples t-test of subjects completing trial 1 and 2 (data from tables 1 and 4) was conducted to evaluate whether there was a difference in exercise routine time from trial 1 to trial 2 which may have contributed to entering a state of ketosis faster. Analysis revealed no significant difference in the exercise routine from trial 1 (M=47, SD=21.10) to trial 2 (M=47.5, SD=21.59), t(9)=0.0432, p=0.9655 (two-tailed) with difference in means of trial 1 and trial 2 being-0.50 minutes 95% CI [−26.67, 25.67].

Data analysis results indicated that, through two trials, paired subjects were able to reduce the mean time required to enter ketosis by roughly 90% without increasing exercise time through utilizing the present invention in combination with dietary carbohydrate restriction and exercise vs. dietary carbohydrate restriction and exercise alone.

An unpaired samples t-test of subjects completing trial 1 vs subjects completing trial 2 only (data from tables 1 and 5) was conducted utilizing Welch's method. The goal of the test was to evaluate the time required to enter ketosis for subjects completing exercise and restricting dietary carbohydrate vs. subjects completing exercise, restricting dietary carbohydrate, and receiving the present invention. The subjects from trial 1 functioned as controls and were compared to subjects who completed trial 2 only. There was a statistically significant difference revealed which was a decrease in the mean time required for unpaired subjects to enter ketosis from trial 1 (M=45.5, SD=13.85) to trial 2 (M=3.77, SD=0.92), t(9)=9.686, p<0.0001 (two-tailed) with a difference in the means of subjects from trail 1 to trial 2 being 41.72 hours, 95% CI [31.98,51.47]. A 41.72 hour reduction in the mean time required to enter ketosis represents roughly a 90% decrease in the total time required to reach ketosis when the present invention is used in combination with exercise and carbohydrate restriction as opposed to dietary carbohydrate restriction and exercise alone.

An unpaired samples t-test of subjects completing trial 1 vs subjects completing trial 2 only (data from tables 1 and 5) was conducted utilizing Welch's method. The goal of the test was to evaluate whether there was a difference in exercise routine time completed by subjects from trial 1 vs subjects from trial 2. The subjects from trial 1 functioned as controls and were compared to subjects who completed trial 2 only. Analysis revealed no significant difference in exercise routine time for unpaired subjects from trial 1 (M=47, SD=21.10) to trial 2 (M=54.1 minutes, SD=33.3), t(13)=0.5482, p=0.5928 (two-tailed) with the difference in means of trial 1 subjects and trial 2 subjects being 7.1 minutes, 95% CI [−35.07,20.89]. Of note was that one subject an 85 year old female entered ketosis in 315 minutes or 5.2 hours with administration of two doses of the present invention without completing any exercise.

Data analysis results indicated that, through two trials, unpaired subjects were able to reduce the mean time required to enter to ketosis by roughly 90% without increasing exercise time through utilizing the present invention in combination with dietary carbohydrate restriction and exercise vs. dietary carbohydrate restriction and exercise alone.

Part of trial 2 was the evaluation of the efficacy of the present invention (therapy) to induce a state of ketosis vs. a placebo in subjects of two randomized groups who restricted carbohydrates and exercised. In group 1, the nine subjects who received the therapy entered ketosis while the three subjects receiving the placebo did not. One subject dropped out for personal reasons and was not included in data analysis. In group 2, the ten subjects who received the therapy entered ketosis while the two subjects receiving the placebo did not. One subject was found to have a positive urine ketone test prior to beginning the trial and was excluded from participating. Of the 26 total subjects randomized to two groups all nineteen subjects who received the therapy as part of the study entered ketosis, the five subjects who received the placebo did not enter ketosis, one subject dropped out, and one subject was excluded.

An unpaired samples t-test of the two randomized, placebo controlled groups was conducted utilizing Welch's method (data from tables 2 and 3). The goal of the test was to evaluate whether there was a difference in the time required to enter ketosis between groups 1 and 2. The nine subjects from group 1 who reached a state of ketosis were compared to the ten subjects from group 2 who also reached a state of ketosis. No significant statistical difference was seen in the mean time required to enter ketosis for group 1 (M=4.2 hours SD=1.93) vs. group 2 (M=3.77, SD=0.92), t(10)=1.50, p=0.1633 (two-tailed) with the difference in the means between group 1 and group 2 being 1.06, 95% CI [−0.51,2.62].

An unpaired samples t-test of the two randomized, placebo controlled groups was conducted utilizing Welch's method (data from tables 2 and 3). The goal of the test was to evaluate whether there was a difference in exercise routine time completed by subjects from group 1 vs. group 2. The nine subjects from group 1 who reached a state of ketosis were compared to the ten subjects from group 2 who also reached a state of ketosis. No significant statistical difference was seen in the exercise routines in group 1 (M=58.3, SD=31.86) vs. group 2 (M=43.7, SD=21.50), t(15)=1.189, p=0.2560 (two-tailed) with the difference in the means between group 1 and group 2 being 14.6, 95% CI [41.75, 40.95]

Data analysis results indicated that there was no significant statistical difference in time required to reach ketosis or exercise routine time for individuals from group 1 vs. group 2 attempting to enter ketosis using the present invention in combination with dietary carbohydrate restriction and exercise.

Taken in whole these results conclude that the present invention, when used in combination with dietary carbohydrate restriction and exercise, drastically reduces the time required to enter a state of endogenous ketone production.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

I claim:

1. A composition for rapidly inducing a state of endogenous ketosis when the composition is accompanied with carbohydrate restriction in a maximum dosage of about 20 grams per day by a user, the composition comprising:
 about 26.66-28.57 percent by mass of alpha lipoic acid;
 about 0.01-0.02 percent by mass of chromium picolinate;
 about 47.61-49.99 percent by mass of L-arginine; and
 about 23.33-23.81 percent by mass of calcium carbonate.

2. The composition of claim 1, wherein the composition comprises zero percent by mass of carbohydrate.

3. The composition of claim 1, wherein the composition comprises zero percent by mass of ketones.

4. The composition of claim 1, wherein the composition comprises zero percent by mass of beta-hydroxybutyrate.

5. The composition of claim 1, wherein a sum total weight of the alpha lipoic acid, the chromium picolinate, the L-arginine, and the calcium carbonate is from 2100.2 to 3000.5 mg.

6. The composition of claim 1, wherein the composition consists of the alpha lipoic acid, the chromium picolinate, the L-arginine, the calcium carbonate, and wherein the composition is compounded by mixing the alpha lipoic acid, the chromium picolinate, the L-arginine, and the calcium carbonate with one or more of sweeteners, flavoring agents, coloring agents, preservatives, pharmaceutically acceptable excipients, binding agents, and lubricating agents.

7. The composition of claim 6, wherein the composition is a compounded into a compounded form selected from the group consisting of a powdered mixture, a pre-mixed drinkable liquid, a tablet, a gelatin capsule, and a concentrated gel.

8. A composition for rapidly inducing a state of endogenous ketosis when the composition is accompanied with carbohydrate restriction in a maximum dosage of about 20 grams per day by a user, the composition comprising:
 600 to 800 mg of alpha lipoic acid;
 200 to 500 micrograms of chromium picolinate;
 1000 to 1500 mg of L-arginine; and
 500 to 700 mg of calcium carbonate.

9. The composition of claim 8, wherein the composition comprises zero grams of carbohydrates.

10. The composition of claim 8, wherein the composition comprises zero grams of ketones.

11. The composition of claim 8, wherein the composition comprises zero grams of beta-hydroxybutyrate.

12. The composition of claim 8, wherein the composition consists of the alpha lipoic acid, the chromium picolinate, the L-arginine, the calcium carbonate, and wherein the composition is compounded by mixing the alpha lipoic acid, the chromium picolinate, the L-arginine, and the calcium carbonate with one or more of sweeteners, flavoring agents, coloring agents, preservatives, pharmaceutically acceptable excipients, binding agents, and lubricating agents.

13. The composition of claim 12, wherein the composition is a compounded into a compounded form selected from the group consisting of a powdered mixture, a pre-mixed drinkable liquid, a tablet, a gelatin capsule, and a concentrated gel.

14. A method for rapidly inducing a state of endogenous ketosis when accompanied with carbohydrate restriction in a maximum dosage of about 20 grams per day by a user, the method comprising:
 restricting carbohydrate consumption to the maximum dosage of about 20 grams per day; and,
 consuming a composition comprising:
  600 to 800 mg of alpha lipoic acid;
  200 to 500 micrograms of chromium picolinate;
  1000 to 1500 mg of L-arginine; and
  500 to 700 mg of calcium carbonate.

15. The method of claim 14, wherein said carbohydrate restriction of the maximum dosage of about 20 grams is prior to consumption of the composition.

16. The method of claim 15, wherein the consumption of the composition is on an empty stomach.

17. The method of claim 14, wherein about thirty minutes after consumption of the composition the user performs moderate intensity exercise.

18. The method of claim 14, wherein about three hours after consuming a first dose of the composition, the user tests for a presence of ketones in urine utilizing at least one sodium nitroprusside urine ketone reagent strip.

\* \* \* \* \*